United States Patent [19]
Kitakado

[11] Patent Number: 5,144,132
[45] Date of Patent: Sep. 1, 1992

[54] METHOD OF AND DEVICE FOR COMPENSATING FOR READING-POSITION ERROR OF IMAGE SENSOR

[75] Inventor: Ryuji Kitakado, Kyoto, Japan

[73] Assignee: Dainippon Screen Mfg. Co., Ltd., Japan

[21] Appl. No.: 734,926

[22] Filed: Jul. 24, 1991

[30] Foreign Application Priority Data

Jul. 27, 1990 [JP] Japan .................................. 2-200673

[51] Int. Cl.$^5$ ...................... H04N 1/028; H04N 1/387
[52] U.S. Cl. ................................. 250/208.1; 358/406; 358/483
[58] Field of Search ............... 358/212, 214, 216, 406, 358/474, 482, 483, 498, 75; 250/208.1

[56] References Cited

U.S. PATENT DOCUMENTS

| 4,691,114 | 9/1987 | Hasegawa et al. | 358/482 X |
| 4,821,110 | 4/1989 | Murakami | 358/495 |
| 4,999,717 | 3/1991 | Nagashima | 358/474 X |
| 5,075,539 | 12/1991 | Shiraishi | 250/208.1 |

Primary Examiner—Constantine Hannaher
Assistant Examiner—Edward J. Glick
Attorney, Agent, or Firm—Ostrolenk, Faber, Gerb & Soffen

[57] ABSTRACT

A device for inspecting a printed board has linear image sensors. The image sensors read the image of the printed board on respective image reading positions (CA0, CB0, CA1, CB1), while scanning the image. A predetermined tolerance range (RY) for image-reading positions is previously determined so that the respective image reading positions are included in the tolerance range. Image signals obtained in respective image sensors are delayed by respective delay times. The respective delay times are previously determined in proportion to the deviations between the image reading positions and a reference position (RLY1), where the reference position is defined on the rear end (EPY1) or behind the tolerance range in the scanning direction (−Y). Through the delay process, all of the image signals are corrected to compensate for the respective deviations in the image reading positions.

16 Claims, 20 Drawing Sheets

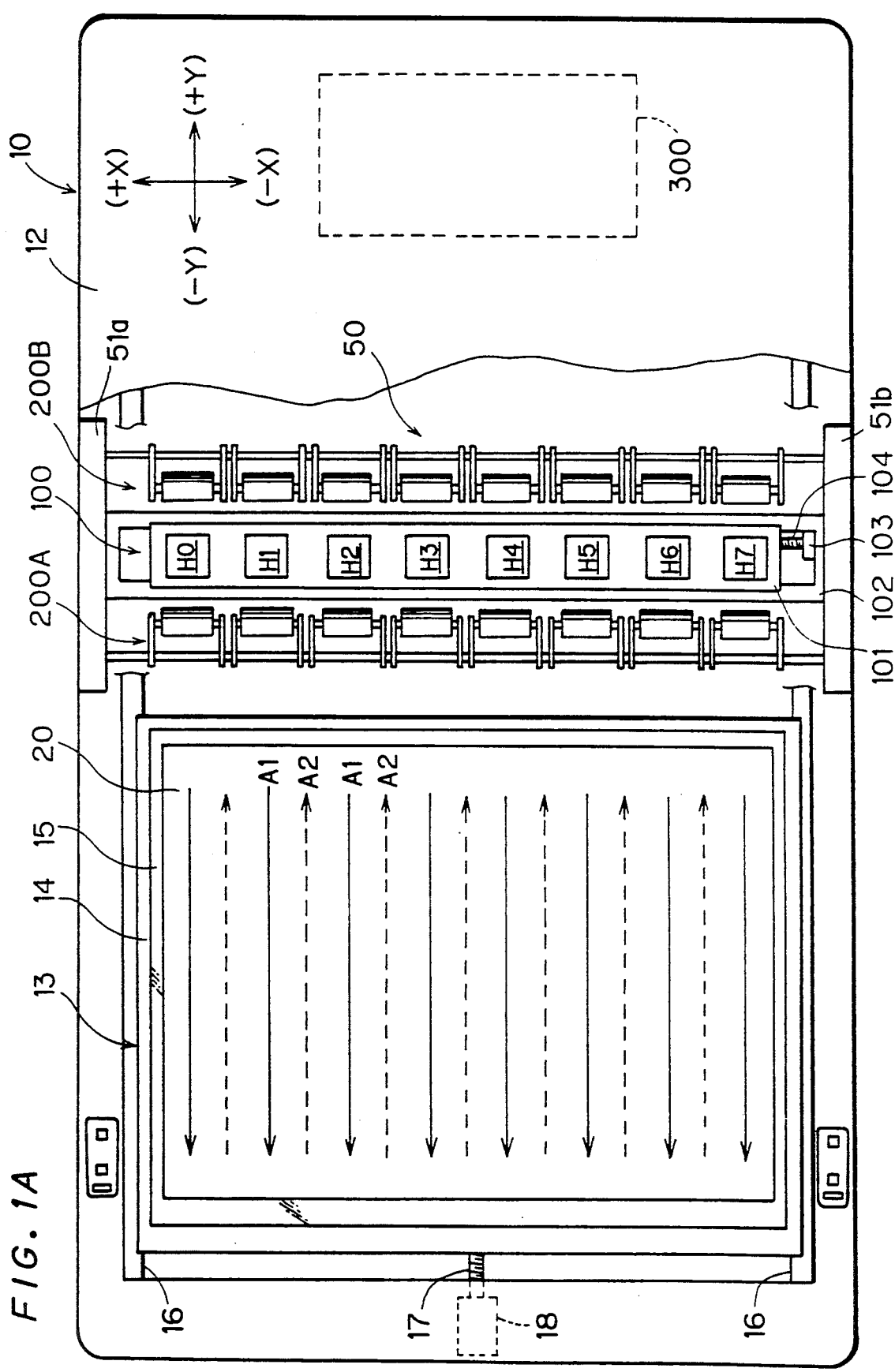

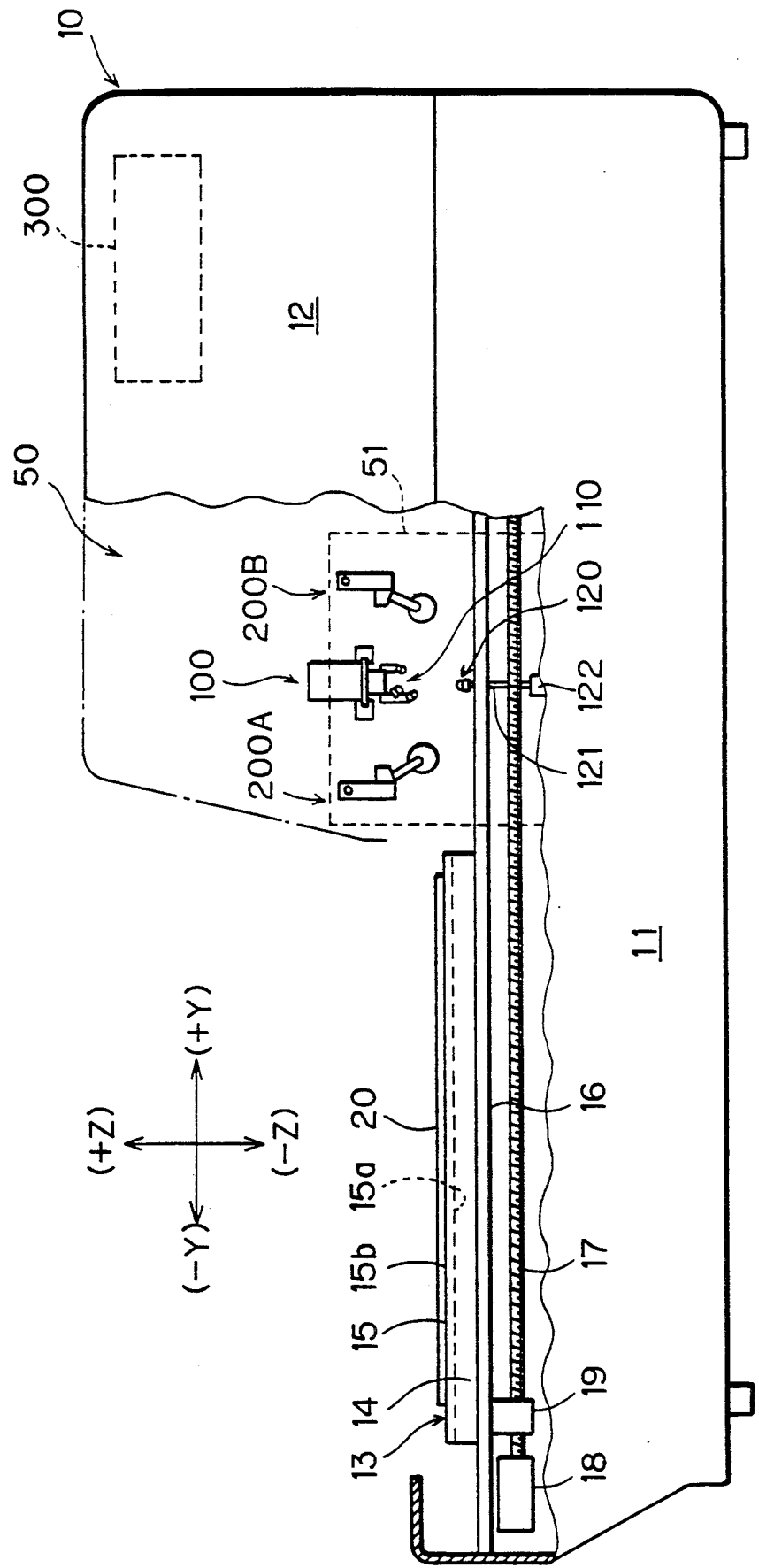

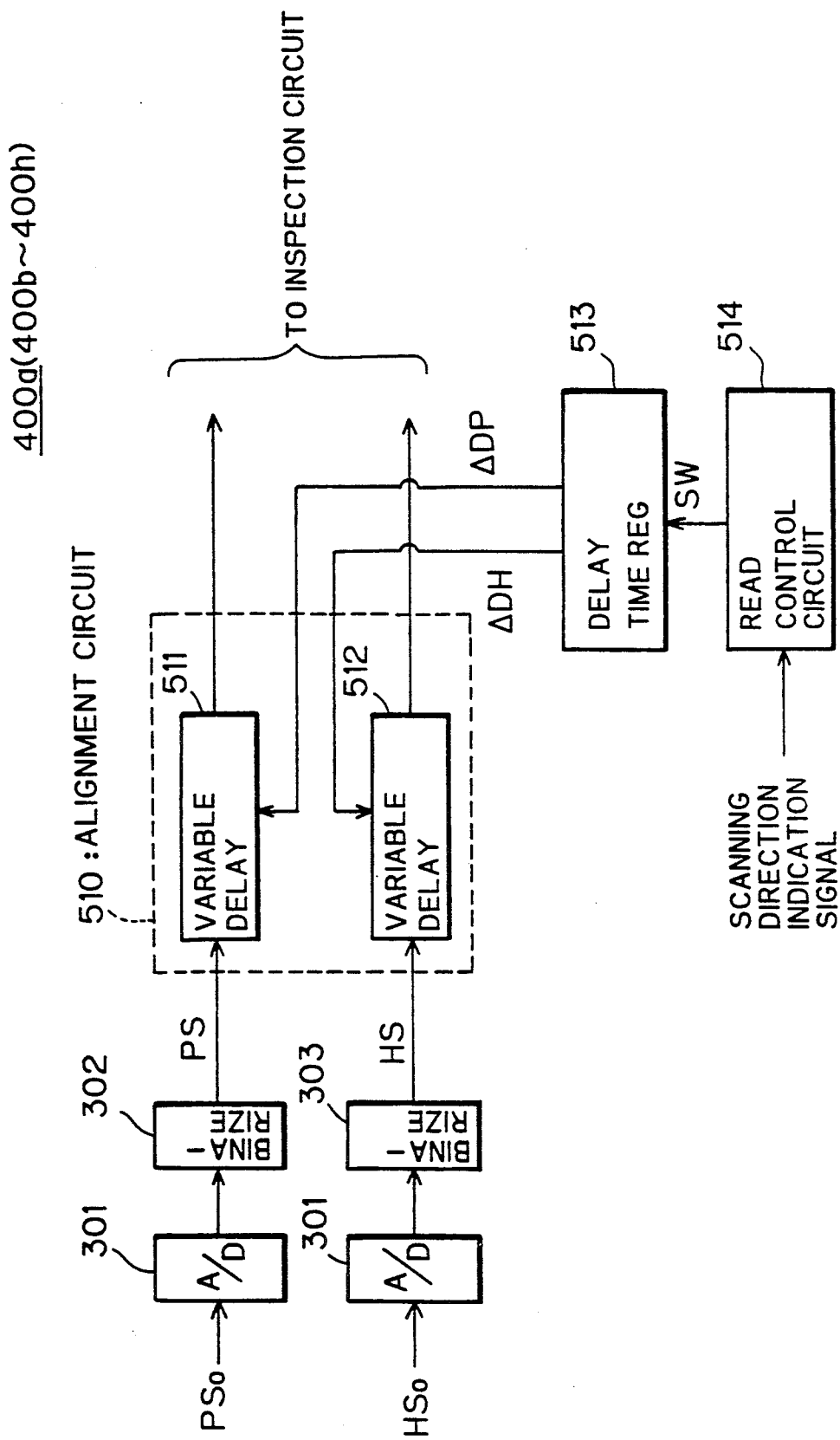

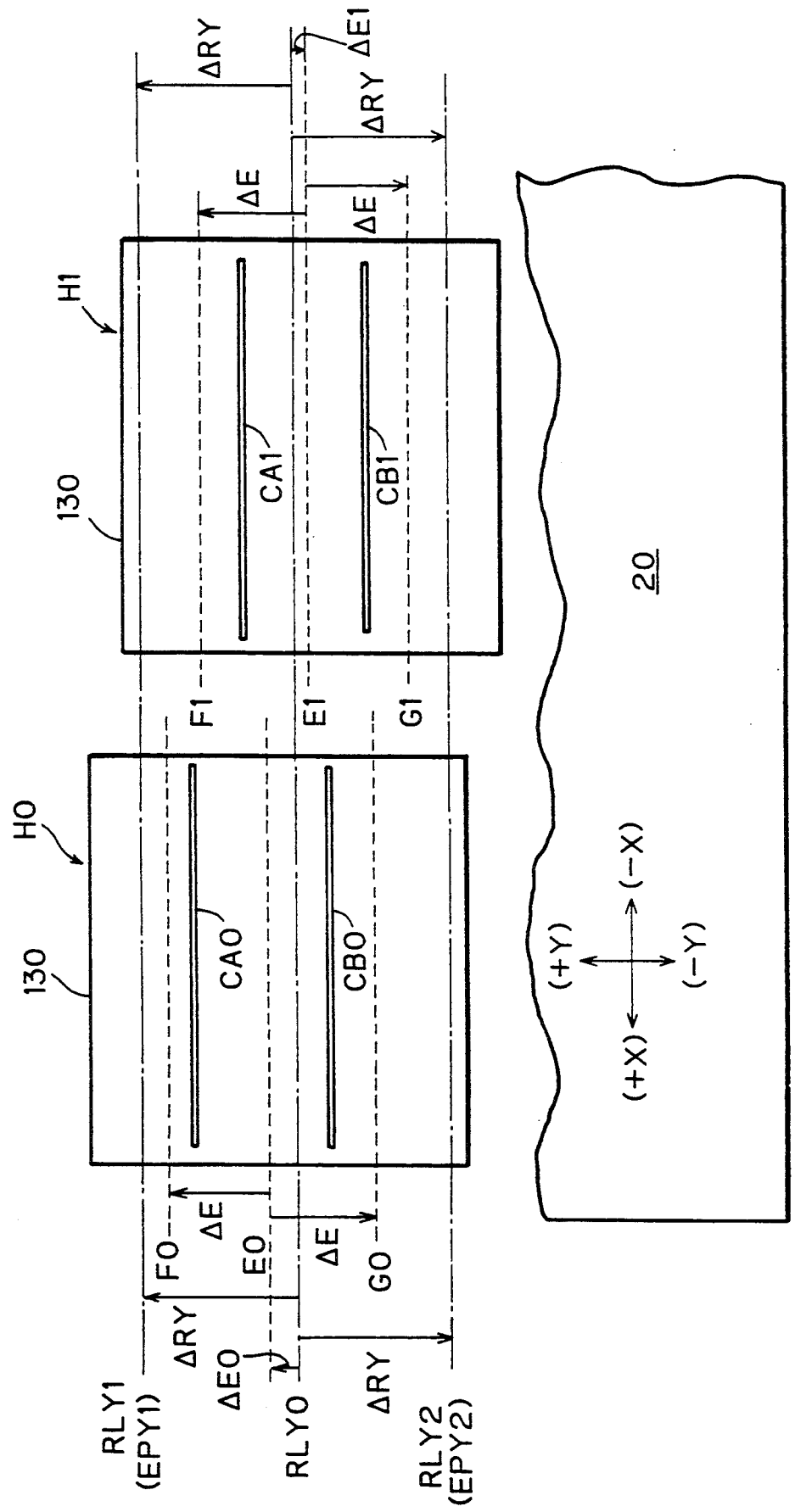

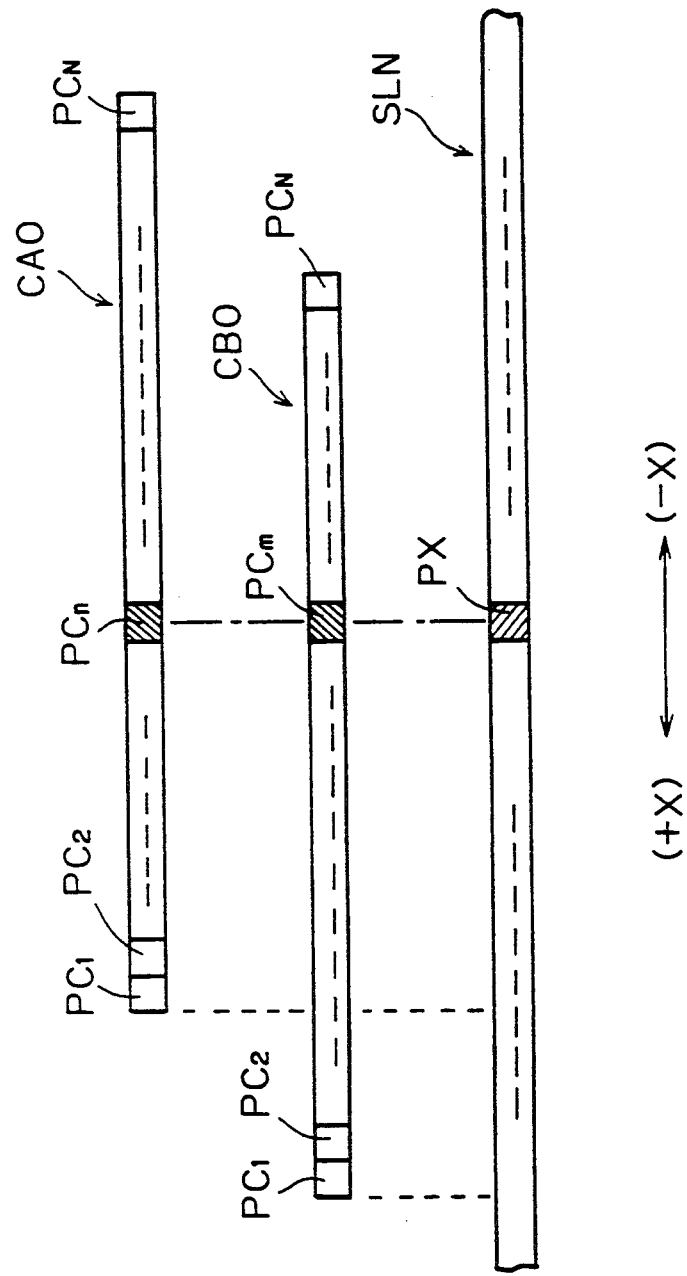

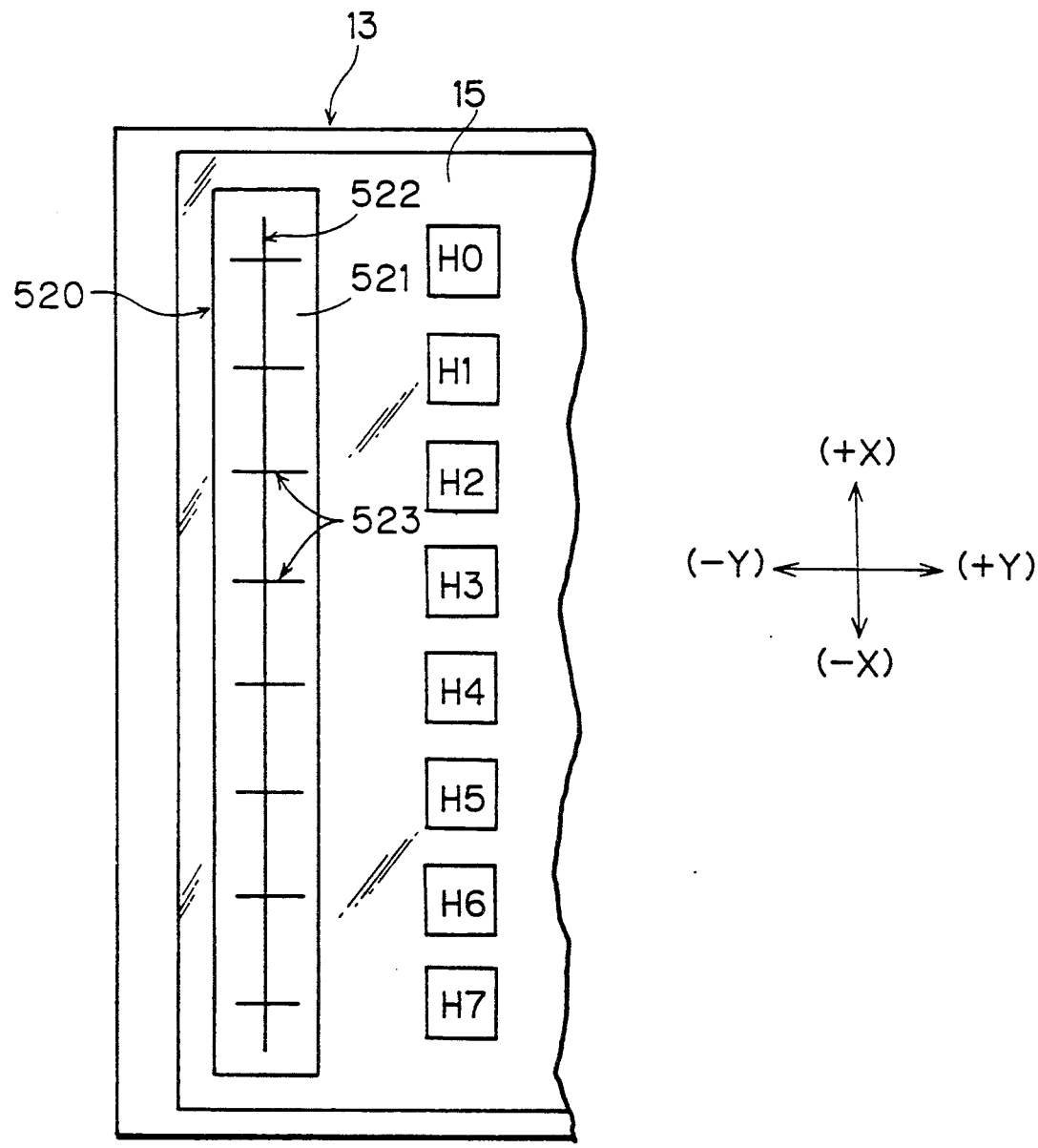

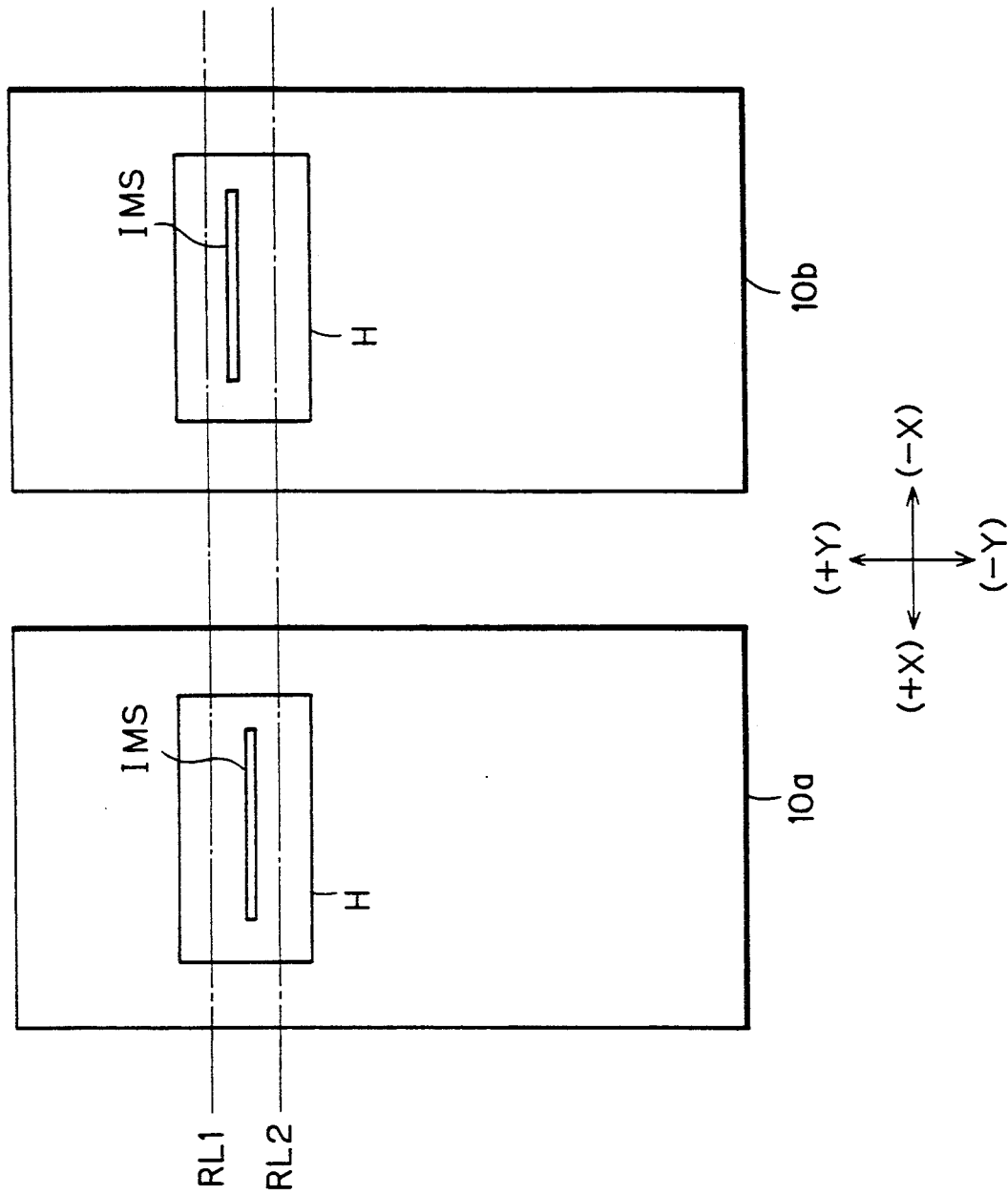

METHOD OF AND DEVICE FOR COMPENSATING FOR READING-POSITION ERROR OF IMAGE SENSOR

BACKGROUND OF THE INVENTION

1. Field of the Invention

The present invention relates to a method of and a device for compensating for a reading-position error of an image sensor, and it also relates to an improved image scan reader and an improved device for inspecting a pattern of a printed circuit board.

2. Description of the Background Art

Printed circuit boards are employed in the field of electronic engineering for mounting and interconnecting electronic elements, and are provided with conductive wiring patterns on one or both sides of insulating boards and with a large number of through holes piercing the insulating boards. Various types of optical visual inspection devices or pattern inspection devices have been employed in order to inspect whether or not the conductive pattern and the through holes are formed accurately within a tolerance.

FIG. 18 is a schematic view of an optical head 951 used for a pattern inspection device of this type. The optical head 951 includes a linear image sensor 952 and an image-formation lens system 953. A printed circuit board 950 and the linear image sensor 952 are moved relatively, and thereby the image of the printed circuit board 950 can be read for each scanning line.

FIG. 19 shows a pattern inspection device of a multichannel type in plan view. As shown in FIG. 19, a printed circuit board 950 is placed on a movable table 954. The device is provided with a plurality of optical heads 951a to 951c having the same structure as the optical head 951 of FIG. 18. The optical heads 951a to 951c read an image while the movable table 954 is transferred in the ($-\alpha$) direction. Accordingly, the image of the printed circuit board 950 is read serially in the direction $\alpha$.

Positions 952a to (52c which image sensors in the optical heads 951a to 951c read at the same time (hereinafter referred to as "reading-positions") are not on a straight line, because of the mounting errors of the image sensors in the optical heads 951a to 951c and/or because of errors in mounting the optical heads 951a to 951c to an optical head support frame. Such errors because the reading-positions 952a to 952c cause a time lag between image signals outputted from the optical heads 951a to 951c, so that accurate image information cannot be obtained.

Hence, there arises a necessity for compensating for the reading-position errors.

Conventionally, the reading-position errors have been compensated in a manner described below. The hindmost reading-position 952b as viewed in the $\alpha$ direction is taken as a reference position PR, to measure positional deviations $e_a$ and $e_c$ of the other reading-positions 952a and (52c from the reference position PR. Signals outputted from the optical heads (51a and 951c are delayed for the times corresponding to the position deviations $e_a$ and $e_c$, respectively. Through this processing, obtained is a condition equivalent to the imaginary state that all of the linear image sensors read the image of the printed board 950 at the reference position PR.

In such a pattern inspection device for printed circuit boards, the image which is obtained by the optical heads 951a to 951c or the image obtained by processing the read image is stored in a storage medium. The image of a printed circuit board having no pattern defects is delivered to other devices of the same type through the storage medium, and is employed therein as a reference image for a pattern comparative inspection and the like.

It is therefore preferable that the image obtained by one device is employed intactly in other devices. That is, the interchangeability of image information is necessary among a plurality of devices.

In the conventional method, however, each device sets the reference position PR individually. This is because the hindmost reading-position as viewed in the scanning direction $\alpha$ depends on the mounting error inherent in each of the devices. The conventional method has not accomplished the aforesaid interchangeability sufficiently. When the image information is transmitted from one device to another device, the conventional method needs position correction in accordance with the relative shift of the reference position for each device.

A similar problem arises where each of the optical heads includes a plurality of image sensors. Even when the reading-position errors are compensated in each optical head, the errors are not compensated in relation to other optical heads. The matching of the image informations provided by the respective optical heads cannot be ensured.

The problem of the interchangeability of the image informations occurs also between the pattern inspection devices each having a single image sensor. The image information obtained in one device cannot be used intactly in other devices because of variation in the mounting position of the image sensor.

Not only the pattern inspection device for the printed circuit board but also various image scan readers have the above-mentioned problems in common.

SUMMARY OF THE INVENTION

The present invention is directed to a method of compensating for a positional error in reading an image of an objective material with an image scan system having at least one image sensor. The image scan system is operable to read the image while scanning the objective material in an image-scanning direction.

According to the present invention, a positional tolerance range for an image reading position of the image sensor is determined on the image scan system. The image reading position of the image sensor is included in the positional tolerance range, and the positional tolerance range has such a front end and a rear end that a direction from the rear end to the front end is in parallel with the image-scanning direction.

Then, a reference position is determined on the rear end or behind the rear end with respect to the image-scanning direction. A positional deviation between the image reading position of the image sensor and the reference position is measured.

Then, the image of the objective material is read with the image sensor while scanning the objective material in the image-scanning direction, to thereby obtain an image signal representative of the image of the objective material. The image signal is delayed by a delay time proportional to the positional deviation to compensate for a positional error in reading the image of the objective material.

In a preferred embodiment of the present invention, the positional tolerance range is determined so that the positional tolerance range is symmetrical with respect to a pre-designed ideal image reading position of the image sensor. The deviation between the image reading position of the image sensor and the reference position may be measured with a sheet member on which a line mark is provided. In this case, the image of the sheet member is read with the image sensor, and obtained is the distance between a position of the line mark in the image of the sheet member and a position of the line mark which is predetermined under the assumption that the image reading position of the image sensor is just on the pre-designed ideal image reading position. The distance thus obtained represents the deviation between the image reading position of the image sensor and the reference position.

In an aspect of the present invention, the method is applied to a system for reading an image of an objective material while scanning the same in main scanning and subscanning directions. In accordance with the condition that the image scanning is conducted in two directions, first and second positional tolerance ranges for an image reading position of the image sensor are determined in the main scanning and subscanning directions, respectively.

A front end and a rear end are defined for each positional tolerance range, and a reference position for each scanning direction is provided on or behind the corresponding rear end. The deviations between the image reading position and the reference positions in respective scanning directions are obtained and are employed for calculating delay time values for respective scanning directions. The respective delay time values are summed up to obtain a delay time, by which the image signal is delayed.

The present invention is also directed to an image scan reader for reading an image of an objective material while scanning the objective material in an image-scanning direction.

According to the present invention, the image scan reader comprises: (a) at least one image sensor for reading the image of the objective material to obtain an image signal representative of the image of the objective material; and (b) delay means for delaying the image signal by a predetermined delay time to obtain a delayed image signal in which a positional error in reading the image of the objective material is compensated for.

A positional tolerance range for an image reading position of the image sensor is previously determined on the image scan reader. The positional tolerance range has such a front end and a rear end that a direction from the rear end to the front end is in parallel with the image-scanning direction. A reference position is previously determined on the rear end or behind the rear end with respect to the image-scanning direction. The delay time is previously determined as a function of a positional deviation between the image reading position of the image sensor and the reference position.

The present invention may be applied to a device for inspecting a printed board. The device comprises one or more image sensors for reading the conductive pattern and the through holes. The image signals obtained in the image sensors are delayed in the same principle as the above-indicated method to compensate the positional error in reading the images of the conductive patterns and the through holes. The device may comprises a plurality of optical heads.

In the pattern inspection by reciprocating scanning, a reference position for going-scan and a reference position for return-scan may be set separately.

According to the present invention, the delayed image signal is provided at a timing equivalent to that just as the respective image sensors read the image at the reference position. The reference position can be set in common to devices of the same type. In a multi-channel device, it can be set in common to channels. Therefore, the image signal obtained by the method and device of the present invention is excellent in interchangeability and matching.

Inasmuch as the reference position is set on the rear end of or behind the tolerance of the reading-position of the image sensor, the reading-position of the image sensor is not shifted behind the reference position. Therefore, the read position constantly lies ahead of the reference position, so that timing adjustment is executable by the aforesaid delay processing.

Accordingly, an object of the present invention is to compensate for a reading-position error while improving interchangeability and matching of image information.

Another object of the present invention is to provide an image scan reader and a device for inspecting a pattern of a printed circuit board, in which interchangeability and matching of image information is attained.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1A is a plan view, with portions broken away, of a pattern inspection device for a printed circuit board according to a preferred embodiment of the present invention;

FIG. 1B is a side view, with portions broken away, of the device of FIG. 1A;

FIG. 6 is a partial block diagram of an inspection circuit unit;

FIGS. 8A and 8B illustrate the principle of compensation for the reading-position error in a sub-scanning direction;

FIGS. 9A to 9C illustrate the principle of compensation for the reading-position error in a main scanning direction;

FIGS. 10A and 10B illustrate a scale plate used for measuring the reading-position error;

FIGS. 13 to 17 illustrate other preferred embodiments of the present invention, respectively;

DESCRIPTION OF THE PREFERRED EMBODIMENTS

A. Structure

Figure 2:
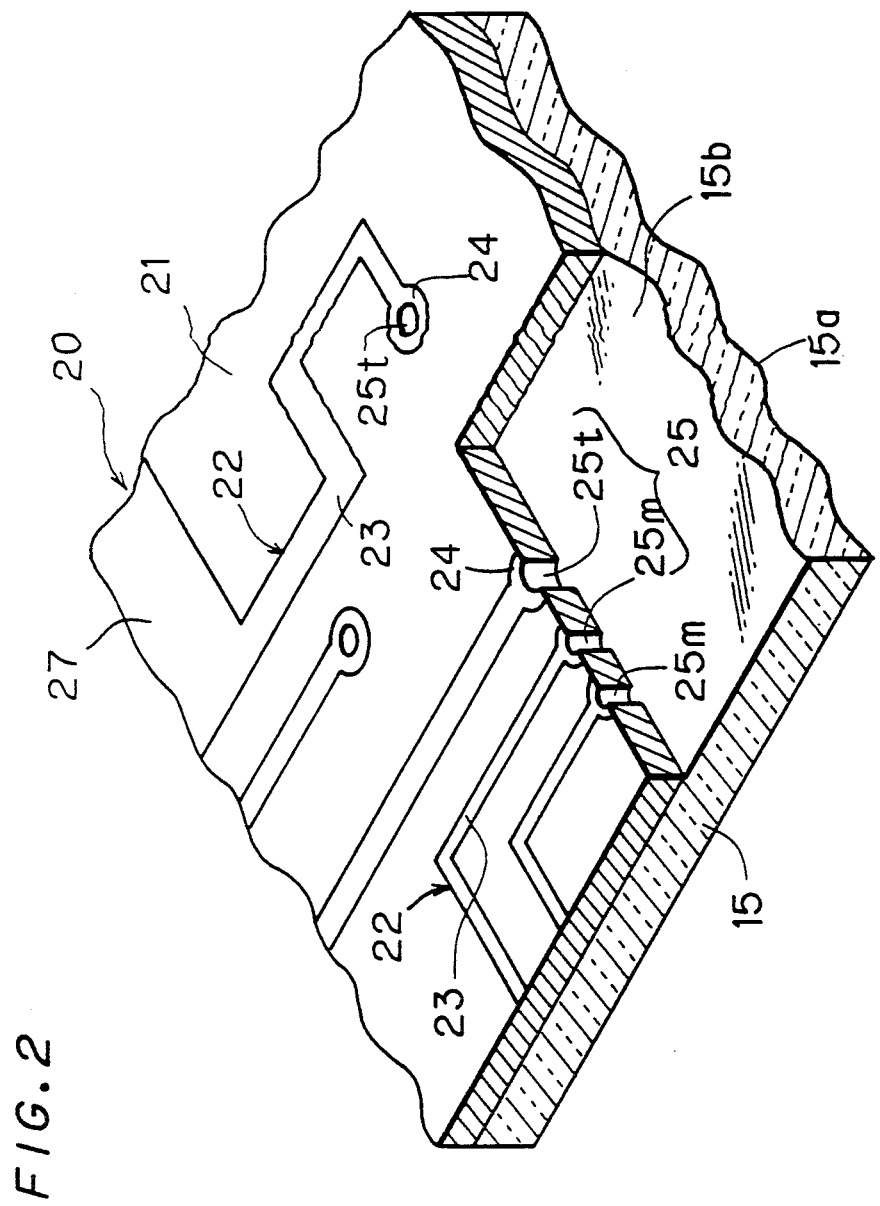
FIG. 2 shows an example of the printed circuit board.

FIG. 1A is a plan view, with portions broken away, of a printed circuit board inspection device 10 according to a preferred embodiment of the present invention, and FIG. 1B is a side view thereof. The device 10 comprises a lower housing 11 and an upper housing 12. The lower housing 11 is provided with a horizontally movable table 13 in the vicinity of an opening on the top surface thereof. The movable table 13 includes a rectangular frame 14 and a glass plate 15 mounted in the rectangular frame 14. The bottom surface 15a of the glass plate 15 is frosted or coarsely ground. A printed circuit board 20 is placed on the top surface 15b of the glass plate 15 and is supported by the glass plate 15.

With reference to FIG. 2, the printed circuit board 20 includes an insulative base plate 21 made of glass epoxy and printed patterns or conductive patterns 22 of copper formed on both surfaces thereof by means of screen printing technique or photo-etching technique. The printed patterns 22 has wiring pattern portions 23, lands 24, and a shield portion 27. Each of the lands 24 is formed therein with a through hole 25 which pierces or penetrates through the printed circuit board 20. The through holes 25 are classified into two types, normal through holes 25t and mini via holes 25m. The normal through holes 25t, having a relatively large diameter, are used for mounting electronic elements and for connecting the electronic elements of the conductive patterns 22. The mini via holes 25m, having a relatively small diameter, is used for electrical connection between the both surfaces of the insulative base plate 21. The inner wall surfaces of the through holes 25t and 25m are plated with conductive metal.

Reference is made again to FIGS. 1A and 1B. The frame 14 is slidable on a pair of guide rails 16. A ball screw 17 extends in the direction parallel to the guide rails 16. A nut 19 fixed to the frame 14 is coupled with the ball screw 17. When a motor 18 turns the ball screw 17, the movable table 13 moves in the horizontal ($\pm Y$) directions.

An image reading system 50 is provided in the upper housing 12. An optical head array 100 extending in the horizontal ($\pm X$) directions is disposed in a space over the mid portion of the image reading system 50. The optical head array 100 includes eight optical heads H0 to H7, which are supported at equal intervals by a supporting member 101. The supporting member 101 is slidable on a guide member 102 in the ($\pm X$) directions. The guide member 102 is fixed to a pair of side frame members 51a and 51b. The supporting member 101 is coupled to a motor 103 through a nut (not shown) and a ball screw 104. When the motor 103 is driven, the optical heads H0 to H7 can move in the ($\pm X$) directions together with the supporting member 101.

A light source 120 for "transmitted illumination" is disposed under the optical heads H0 to H7, wherein "transmitted illumination" is defined as illumination applied to an object and transmitting through holes formed in the object. The light source 120 is composed of a large number of infrared LEDs arranged in the ("X) directions, and serves substantially as a linear light source. The light source 120 is supported from the side frames 51 through supporting rods 121 and 122. Each of the optical heads H0 to H7 has a light source 110 for "reflected illumination", which light source 110 is attached to the bottom thereof. "Reflected illumination" is defined as illumination applied to an object and reflected at the surface of the object. The light source 110 includes three pairs of one-dimensional arrays of red LEDs extending in the ($\pm X$) directions.

Presser roller mechanisms 200A and 200B are provided on opposite sides of the optical head array 100 in order to press the printed circuit board 20 fed thereunder. The presser roller mechanisms 200A and 200B are operable to prevent the out-of-position and flexure of the printed circuit board 20.

A data processor 300 for performing various data processings and operation controls is disposed in the upper housing 12.

B. Overall Operation

Prior to the description of the detailed structure of the inspection device 10, the overall operation of the device 10 will be discussed hereinafter. Initially, the printed circuit board 20 is placed on the glass plate 15 as shown in FIGS. 1A and 1B. When an operation switch is manually operated, the motor 18 is forwardly rotated so that the printed circuit board 20 moves in the ($\pm Y$) direction together with the movable table 13. The light sources 100 and 120 light up.

Then, the printed circuit board 20 reaches the position of the image reading system 50 with the movement of the table 13. The optical heads H0 to H7 read the images of the printed patterns 22 (of FIG. 2) illuminated by the reflected illumination from the light source 110, while reading the images of the through holes 25 illuminated by the transmitted illumination from the light source 120. Respective image reading are conducted for each scanning line schematically defined on the printed circuit board 20.

Since there is gaps between the visual fields of the respective optical heads H0 to H7 arranged in line, the whole image on the surface of the printed circuit board 20 cannot be read through a movement of the printed circuit board 20 in the ($+Y$) direction. After the movement of the printed circuit board 20 in the ($+Y$) direction, the motor 103 is driven to move the optical heads H0 to H7 in the ($+X$) direction. The distance of the movement in the ($+X$) direction is the half of the mutual arrangement pitch of the optical heads H0 to H7. After this movement, the motor 18 is reversely rotated. Accordingly, the printed circuit board 20 moves in the ($-Y$) direction, while the optical heads H0 to H7 read the remaining parts of the images of the wiring patterns 22 and the through holes 25.

As a result, both scans indicated by the solid arrows A1 and the the broken arrows A2 of FIG. 1A are carried out, whereby the image reading throughout the surface of the printed circuit board 20 can be accomplished. The images detected are given to the data processor 300, in which whether the printed patterns 22 and the through holes 25 are defective or not is decided on predetermined criteria.

C. Details of Optical Heads

Figure 3:
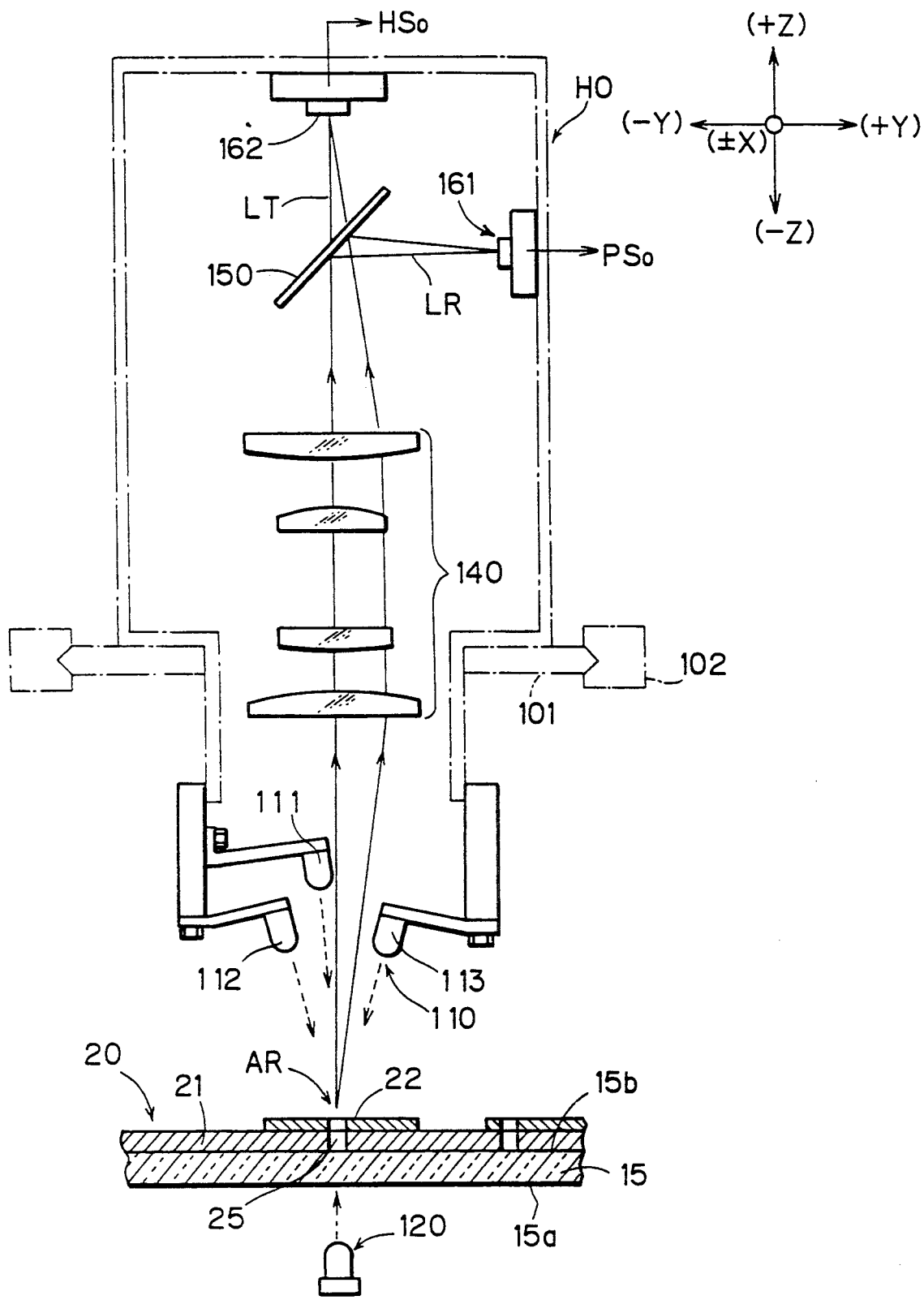
FIG. 3 is a schematic side view of an optical head employed in the preferred embodiment.

FIG. 3 is a schematic side view of the internal structure of the optical head H0, Although FIG. 3 shows only the optical head H0, the other optical heads H1 to H7 have the same structure.

The light source 110 for reflected illumination is composed of a light source 111 for regular reflection and light sources 112 and 113 for irregular reflection. Each of the light sources 111, 112 and 113 is substantially a linear light source composed of a one-dimensional array of red LEDs which generate red light of wavelength $\lambda_1$ (=600 to 700 nm).

Light from the light sources 111, 112 and 113 are applied to an area-to-be-inspected or objective area Ar of the top surface of the printed circuit board 20 which is currently located just under the optical head H0.

The light source 120 for transmitted illumination is composed of a one-dimensional array of infrared LEDs which generate infrared light of wavelength $\lambda_2$ (=700 to 1000 nm). The light source 120 projects the infrared light in the (+Z) direction toward an area corresponding to the reverse side of the area AR in the printed circuit board 20.

Part of the red light generated in the light sources 111, 112 and 113 for reflected illumination reaches the area AR and is reflected at the area AR. Part of the infrared light from the light source 120 for transmitted illumination reaches the through holes 25 and passes through the through holes 25. The reflected light and the transmitted light thus obtained are directed to the optical head H0 as a spatially superposed compound light.

As shown in FIG. 3, the compound light passes through an image-formation lens system 140 and impinges on a cold mirror 150. The cold mirror 150 transmits only infrared rays. The red light (i.e., the reflected light LR from the surface of the printed circuit board 20) included in the compound light is reflected at the mirror 150 to the (+Y) direction so that an image is formed on a photo-detecting surface of a first CCD linear image sensor 161. The infrared light (i.e., the transmitted light LT through the through hole 25) included in the compound light passes through the mirror 150 so that an image is formed on a photo-detecting surface of a second CCD linear image sensor 162.

Each of the CCD linear image sensors 161 and 162 has CCD photo-electric cells arranged one-dimensionally in the ($\pm$X) directions. The first linear image sensor 161 detects the one-dimensional image of the surface of the printed circuit board 20 illuminated by the reflected illumination. The second linear image sensor 162 detects the one-dimensional image of the through hole 25 illuminated by the transmitted illumination. The movement mechanism shown in FIGS. 1A and 1B moves the printed circuit board 20 and the optical head array 100 relatively, thereby each area of the printed circuit board 20 being scanned. The two-dimensional images of the wiring pattern 22 and the through hole 25 for each area can be obtained.

D. Electric Structure and Operation

D-1. Overall Structure

Figure 4:
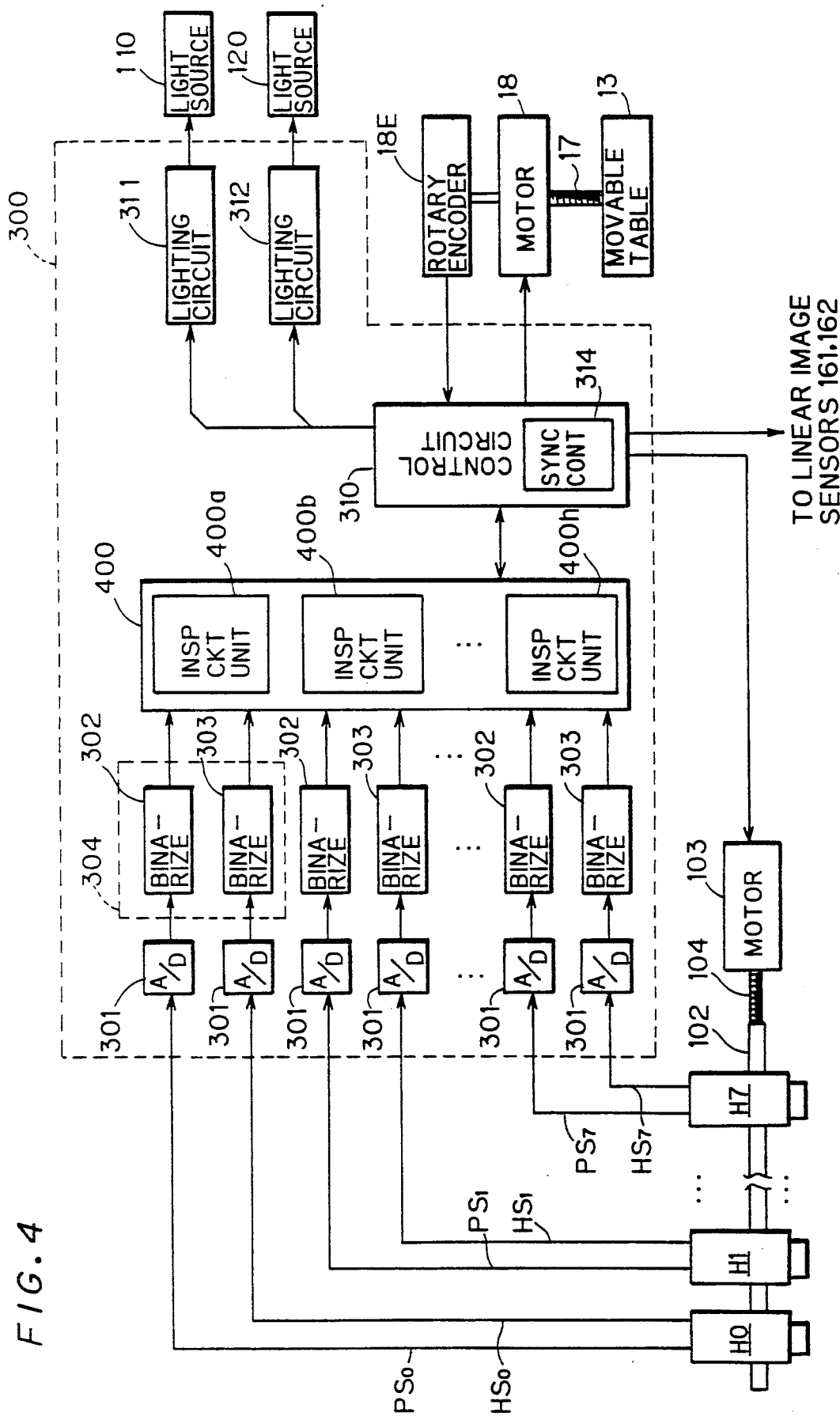
FIG. 4 is a block diagram of the while electric structure of the preferred embodiment.

FIG. 4 is a block diagram of the overall electric structure of the preferred embodiment. A/D converters 301 receive wiring pattern image signals $PS_0$-$PS_7$ and through hole image signals $HS_0$-$HS_7$ from the optical heads H0 to H7, respectively, to convert them into digital signals. The digital signals are transmitted to circuits 304 each composed of binarizing circuits 302 and 303.

Figure 5A:
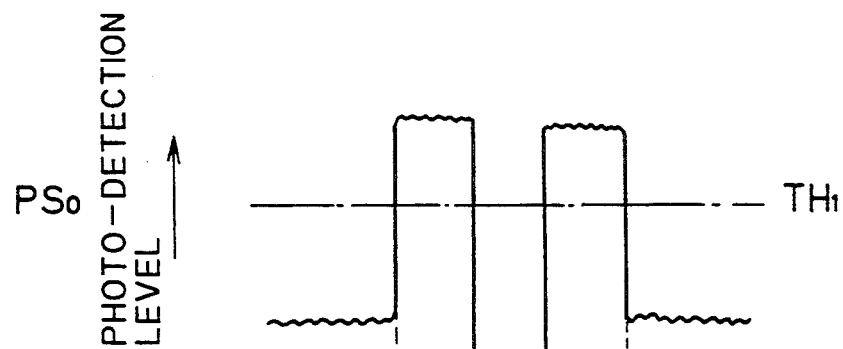
FIG. 5(a) and 5(b) illustrate binarization of a printed pattern and a through hole.
Figure 5B:
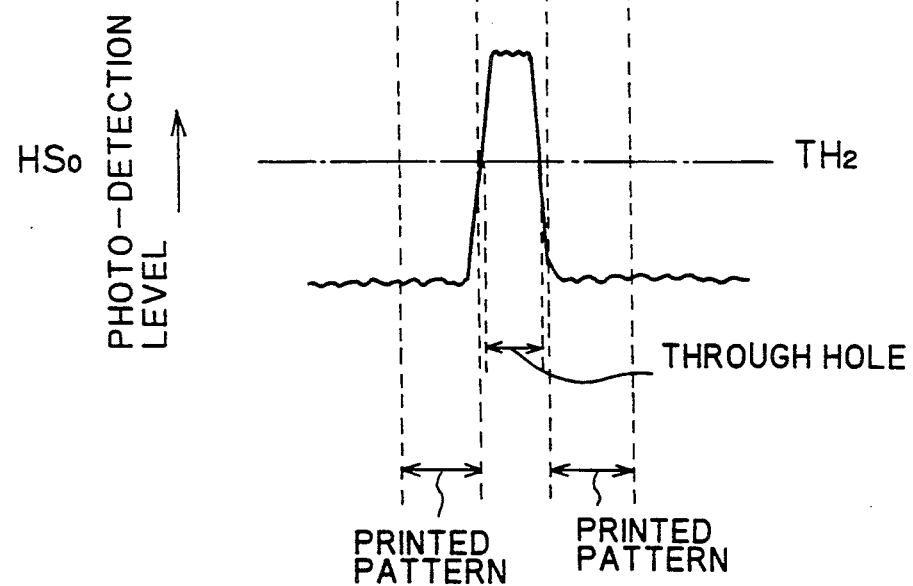

The binarizing circuits 302 and 303 compare the digitized image signals $PS_0$ and $HS_0$ with predetermined threshold values TH1 and TH2 (see FIGS. 5($a$) and 5($b$)) to output binarized signals, respectively. The binarized signals are at a logical "H" level when the levels of the signals $PS_0$ and $HS_0$ are higher than the threshold values TH1 and TH2, while they are at a logical "L" level when the levels of the signals $PS_0$ and $HS_0$ are lower than the threshold values TH1 and TH2, respectively. The binarizing circuits 302 and 303 corresponding to the other optical heads H1 to H7 have the same structure.

The binarized image signals thus obtained are transmitted to a pattern inspection system 400. The pattern inspection system 400 includes eight inspection circuit units 400a to 400h corresponding to the optical heads H0 to H7. The units 400a to 400h construct the two-dimensional images of the printed patterns 22 and the through holes 25 based on the image signals which are supplied from the optical heads H0 to H7 and digitalized in the circuits 302 or 303. The units 400a and 400h are operable to decide whether the printed patterns 22 and the through holes 25 are defective or not on predetermined criteria.

The data processor 300 further comprises a control circuit 310. The control circuit 310 applies turn on/off commands to the light sources 110 and 120 through lighting circuits 311 and 312, and outputs drive control signals to the motors 18 and 103. The motor 18 is equipped with a rotary encoder 18E, which detects a motor rotation angle signal. The motor rotation angle signal for ruling data processing timing is given to the control circuit 310.

The control circuit 310 includes a synchronization control circuit 314 for controlling the read timing of the linear image sensors 161 and 162 and the synchronization of the motors 18 and 103.

D-2. Principle of Compensation for Reading-Position Error

FIG. 6 is a block diagram of an input-side portion of the inspection circuit unit 400a. The other inspection circuit units 400b to 400h have the same structure.

The image signals PS and HS outputted from the binarizing circuits 302 and 303 are given to an alignment circuit 510 as a pattern signal PS and a hole signal HS which represent the two-dimensional images of the printed pattern 22 and the through hole 25, respectively. The alignment circuit 510 compensates for the reading-position errors of the linear image sensors 161 and 162 on a principle common to the optical heads H0 to H7. Prior to the description of the internal structure of the circuit 510, the cause of the reading-position errors in the pattern inspection device 10 of the preferred embodiment and the principle of compensation for the errors will be discussed below.

Figure 7A:
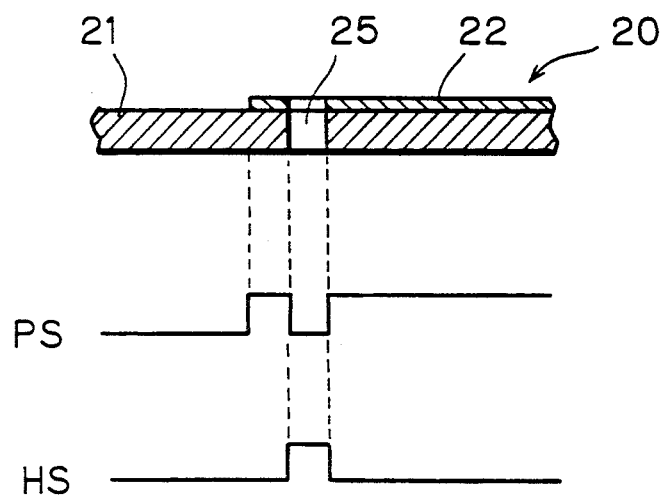
FIGS. 7A and 7B illustrate a reading-position error of a linear image sensor.
Figure 7B:
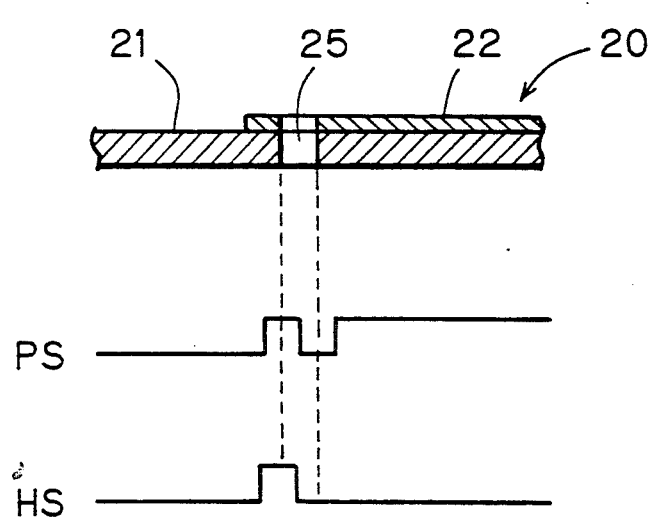

A first cause of the reading-position errors is the mounting errors of the linear image sensors 161 and 162 in the optical head H0 (or H1 to H7). It is ideal that the linear image sensors 161 and 162 detect the reflected light and the transmitted light from the same area AR as shown in FIG. 3. However, the respective practical reading-positions of the linear image sensors 161 and 162 deviate from each other due to the mounting errors. Accordingly, it is difficult, in practice, to achieve the ideal timings shown in FIG. 7A in which the pattern signal PS is perfectly aligned with and the hole signal HS. A phase shift is generated between the signals PS and HS as shown in FIG. 7B.

A second cause of the reading-position errors is errors in mounting the optical heads to the supporting member 101 of FIG. 1A. Such errors cause read errors between the respective optical heads H0 to H7. Both of the first and second causes exert influence on read-timings in the main scanning direction (−X) and the sub-scanning directions (±Y).

FIG. 8A is a schematic plan view illustrating the reading-position errors in the sub-scanning directions (±Y). Although only the optical heads H0 and H1 are shown in FIG. 8A, the other optical heads H2 to H7 have the same situation. In the optical head H0, a reading-position CA0 of the linear image sensor 161 for detecting the reflected light and a reading-position CB0 of the linear image sensor 162 for detecting the transmitted light are shifted from each other in the (±Y) directions. The reading-positions CA0 and CB0 lie within an in-channel tolerance F0 to G0 which has each width $\Delta E$ in the opposite directions (±Y) symmetrically with respect to a zeroth channel reference line E0 determined on a housing 130 for the optical head H0. The width $\Delta E$ has a predetermined value in consideration of the mounting accuracy of the linear image sensors 161 and 162, for example, a width corresponding to eight scanning lines.

The same is true for the optical head H1. An in-channel tolerance F1 to G1 is defined symmetrically with respect to a first channel reference line E1 determined on a housing 130 for the optical head H1. Reading-positions CA1 and CB1 of the linear image sensors 161 and 162 in the optical head H1 lie within the tolerance F1 to G1. As is not shown in FIG. 8A, in-channel tolerances of the remaining optical heads H2 to H7 are defined symmetrically with respect to channel reference lines E2 to E7, respectively.

The channel reference lines E0 to E7 deviate from each other in the (±Y) directions. This deviation results from errors in mounting the housings 130 for the respective optical heads H0 to H7 to the supporting member 101 of FIG. 1A. The allowable width of the errors is defined as $\Delta H$ (not shown) each in the (±Y) directions symmetrically with respect to a system reference line RLY0 determined on the supporting member 101. The system reference line RLY0 is common to the respective optical heads H0 to H7. The absolute values of errors $\Delta E0$ to $\Delta E7$ of the channel reference lines E0 to E7 from the system reference lien RLY0 are not more than the allowable error width $\Delta H$ which is, for example, a width corresponding to one scanning line.

In the preferred embodiment, an allowable error width $\Delta RY$ is defined each in the (±Y) directions symmetrically with respect to the system reference line RLY0, where $$\Delta RY \geq \Delta E + \Delta H \qquad (1)$$

The allowable error width $\Delta RY$, is, for example, a width corresponding to nine scanning lines. A first reference position RLY1 and a second reference position RLY2 are defined, which are spaced $\Delta RY$ apart from the system reference line RLY0 in the (±Y) directions, respectively.

A reading tolerance RY (FIG. 8B) in the sub-scanning direction (hereinafter referred to as a "Y-tolerance") for all of the linear image sensors 161 and 162 included in the image reading system 50 is defined such that a sub-scanning coordinate Y satisfies the following expression (2):

$$RLY0 - \Delta RY \leq Y \leq RLY0 + \Delta RY \qquad (2)$$

Accordingly, the first and second reference positions RLY1 and RLY2 are on respective end positions EPY1 and EPY2 of the Y tolerance RY. The first reference position RLY1 is set for use in a period (hereinafter referred to as a "going-scan period") in which the image of the printed circuit board 20 is scanned in the (−Y) direction in accordance with the conveyance of the printed circuit board 20 in the (+Y) direction. The second reference position RLY2 is set for use in a period (hereinafter referred to as a "return-scan period") in which the image of the printed circuit board 20 is scanned in the (+Y) direction in accordance with the conveyance of the printed circuit board 20 in the (−Y) direction. The first reference position RLY1 lies on the rear end of the Y-tolerance RY as viewed in the scanning direction (−Y), while the second reference position RLY2 lies on the rear end of the Y-tolerance RY as viewed in the scanning direction (+Y).

In the going-scan period, the output signals of the image sensors are delayed for the times corresponding to position deviations $\Delta C_{A0-}$, $\Delta C_{B0-}$, $\Delta C_{A1-}$, $\Delta C_{B1-}$, ... between the first reference position RLY1 and the reading-positions CA0, CB0, CA1, CB1, ... of the linear image sensors included in the optical heads H0 to H7, respectively. In the return-scan period, the output signals of the image sensors are delayed for the times corresponding to position deviations $\Delta C_{A0+}$, $\Delta C_{B0+}$, $\Delta C_{A1+}$, $\Delta C_{B1+}$, ... between the second reference position RLY2 and the reading-positions CA0, CB0, CA1, CB1, ..., respectively. The delay processing provides the image signals at the timings equivalent to those just as all of the linear image sensors read at the first reference position RLY1 in the going-scan period. The second reference position RLY2 becomes such as "equivalent common reading-position" in the return-scan period.

This delay processing has the following characteristics:

(1) Since the reference positions RLY1 and RLY2 are common to the optical heads H0 to H7, the timings of the output signals are adjustable not only between the linear image sensors 161 and 162 in the respective optical heads H0 to H7 but also between the optical heads H0 to H7.

(2) The reference positions RLY1 and RLY2 can be defined at the same positions in other devices of the same type as the pattern inspection device 10. This is because the reference positions RLY1 and RLY2 can be determined independent of the practical reading-positions of respective image sensors.

(3) The reference positions RLY1 and RLY2 are on the rear ends of the Y-tolerance RY as viewed in the respective scanning directions. The reading-positions of the image sensors are sue to be on or ahead of the reference positions RLY1 and RLY2 even if distributed within the Y-tolerance RY. In the going-scan period, for example, the reading-positions CA0, CB0, CA1, CB1, ... are surely on or ahead of the first reference line RLY1 as viewed in the sub-scanning direction (−Y). They never lie behind the first reference line RLY1. Hence, the execution of the delay processing on the output signals of the image sensors permits the timings to be adjusted at the reference position RLY1. The first reference position RLY1 may be set behind the Y-tolerance as viewed in the sub-scanning direction (−Y) in the going scan period, that is, in a region satisfying:

$$Y > RLY0 + \Delta RY \quad (3)$$

Similarly, the second reference position RLY2 may be set behind the Y tolerance as viewed in the sub-scanning direction (+Y) in the return-scan period, that is, in a region satisfying:

$$Y < RLY0 - \Delta RY \quad (4)$$

Supposing that the first reference position RLY1 is set within or ahead of the Y-tolerance RY, a time advance must be applied to the output signals of the image sensors in order to adjust the timings at the reference position RLY1. It is impossible, however, to apply the time advance to the image signals in a real-time signal processing while reading images. Therefore, this supposition is unadaptable.

FIG. 9A illustrates the reading-position errors in the main scanning direction. For convenience of description, it is assumed in FIG. 9A that there is no reading-position error in the sub-scanning direction. For the same reason, the reading-positions CA0 and CB0 of the linear image sensors 161 and 162 are shown in FIG. 9A at a distance above a scanning line SLN to be noted.

Supposing that each of the linear image sensors 161 and 162 has N-number of CCD cells (where N is an integer equal to or more than two), each of the reading-positions CA0 and CB0 is composed of the one-dimensional array of read pixels $PC_1$ to $PC_N$ for the N-number of CCD cells. Because of the relative shifts of the reading-positions CA0 and CB0 in the (±X) directions, one pixel PX on the scanning line SLN is read as the n-th read pixel $PC_n$ at the reading-position CA0, while the pixel PX is read as the m-th read pixel $PC_m$ at the reading-position CB0, where $$1 \leq n \leq N, \ 1 \leq m \leq N \quad (4)$$

$$n \neq m, \ n < m \quad (5)$$

Timings at which charges are transferred from the CCD cells ("photo-detection level read-timings") are adapted to be common to the linear image sensors 161 and 162. At the same time that a photo-detection level from the first read pixel $PC_1$ in the reading-position CA0 is read out from the linear image sensor 161, a photo-detection level from the first read pixel $PC_1$ in the reading-position CB0 is read out from the linear image sensor 162. This is because a common reading-start pulse is applied to the linear image sensors 161 and 162.

Figure 9B:
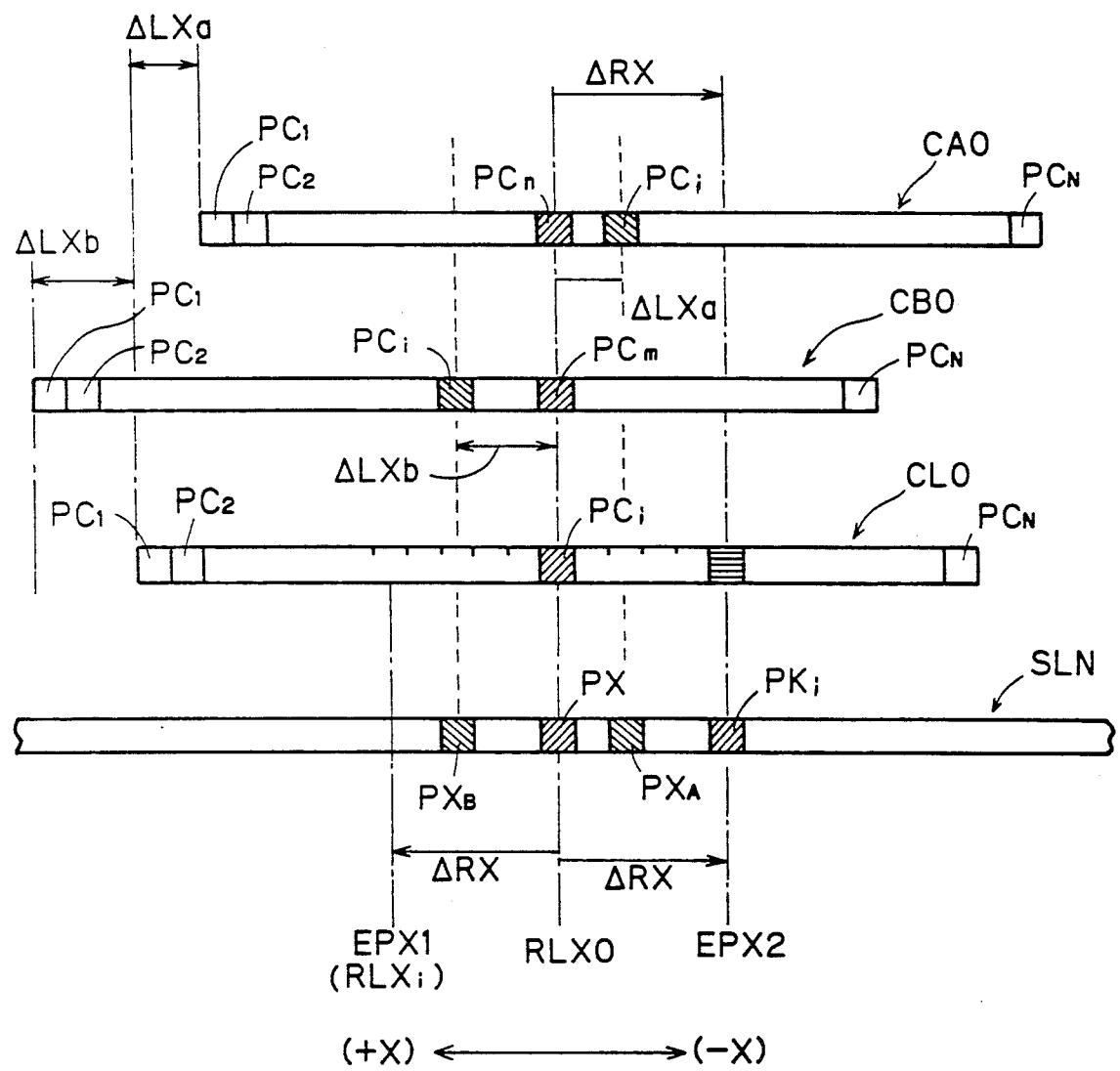

Although the photo-detection levels of the i-th read pixels $PC_i$ in the reading-positions CA0 and CB0 are read out simultaneously as shown in FIG. 9B, the respective read pixels $PC_i$ are not identical to each other on the scanning line SLN on the printed circuit board 20 but correspond to different pixels $PX_A$ and $PX_B$, respectively. That is, at the same time that the photo-detection level of the pixel $PX_A$ is read out from the linear image sensor 161, the photo-detection level of the pixel $PX_B$ is read out from the linear image sensor 162.

The positions of the pixels $PX_A$ and $PX_B$ on the scanning line SLN vary depending on the mounting position errors of the linear image sensors 161 and 162 in the (±X) directions, and the like. However, similarly to the reading-position errors in the sub-scanning direction, a read tolerance in the main scanning direction (or an "X-tolerance") has each maximum error width $\Delta RX$ in the (±X) directions symmetrically with respect to a reference line RLX0 for the i-th pixel $PC_i$ located at the ideal reading position CL0 defined for an imaginary condition that the respective linear image sensors are mounted without errors. Accordingly, the X-tolerance is defined as the range of the X-coordinate values satisfying the following expression (6):

$$RLX0 - \Delta RX \leq X \leq RLX0 + \Delta RX \quad (6)$$

There are shown in FIG. 9B both end positions EPX1 and EPX2 of the expression (6).

The pixel on the scanning line SLN corresponding to the read pixel $PC_i$ is on the end position EPX1 when the reading-positions CA0 and CB0 deviate in the (+X) direction in maximum. Similarly the pixel on the scanning line SLN corresponding to the read pixel $PC_i$ is on the other end position EPX2 when the reading-positions CA0 and CB0 deviate in the (−X) direction in maximum. In this preferred embodiment, accordingly, a reference position $RLX_i$ is determined on the end position EPX1 which corresponds to the rear end of the X-tolerance as viewed in the main scanning direction (−X). The reference position $RLX_i$ is defined for the image sensors. On the other hand, the situation that the image sensors are mounted in positions deviated in the direction (+X), for example, is equivalent to the situation that reading positions on the printed board are deviated in the direction (−X). Thus, on the coordinates fixed to the printed board, a reference position is defined at the other end position EPX2 and the pixel $PK_i$ corresponding thereto is employed as a reference pixel.

In FIG. 9B illustrating a condition related to the preferred embodiment, the reading-position CA0 is deviated from the ideal reading-position CL0 by $\Delta LX_a$ in the direction (−X) while the reading-position CB0 is deviated from the ideal reading-position CL0 by $\Delta LX_b$ in the direction (+X), due to the mounting errors of the linear image sensors 161 and 162. Accordingly, the pixel PX on the scanning line SLN is read as the read pixel $PC_n$ on the reading-position CA0 while the same is read as the read pixel $PC_m$ on the other reading-position CB0, as described with reference to FIG. 9A.

The respective output signals from the read pixels of CCD cells $PC_n$ and $PC_m$ corresponding to the one pixel PX are delayed in a unit of pixels to the position of the reference position $RLX_i = EPX1$ on the coordinates fixed to the image sensors, or to the position of the reference pixel $PK_i$ on the coordinates fixed to the printed board.

The read pixel $PC_n$ is read earlier than the ideal read pixel $PC_i$ by $\Delta LX_a$, and therefore, a delay time $\Delta X_A$ for the read pixel $PC_n$ is determined as $\Delta X_A = \Delta RX + \Delta LX_a$. On the other hand, the other read pixel $PC_m$ is read later than the ideal read pixel $PC_i$ by $\Delta LX_b$, and a delay time $\Delta X_B$ for the read pixel $PC_m$ is determined as $\Delta X_B = \Delta RX - \Delta LX_b$.

This delay processing permits the image signals provided from the linear image sensors 161 and 162 to be matched with each other as far as the deviations of the reading-positions CA0 and CB0 in the main scanning direction are within the X-tolerance. In the image signals after the delay, image data for the same pixel on the scanning line SLN is obtained in the linear image sensors 161 and 162 at the same timing.

Figure 9C:
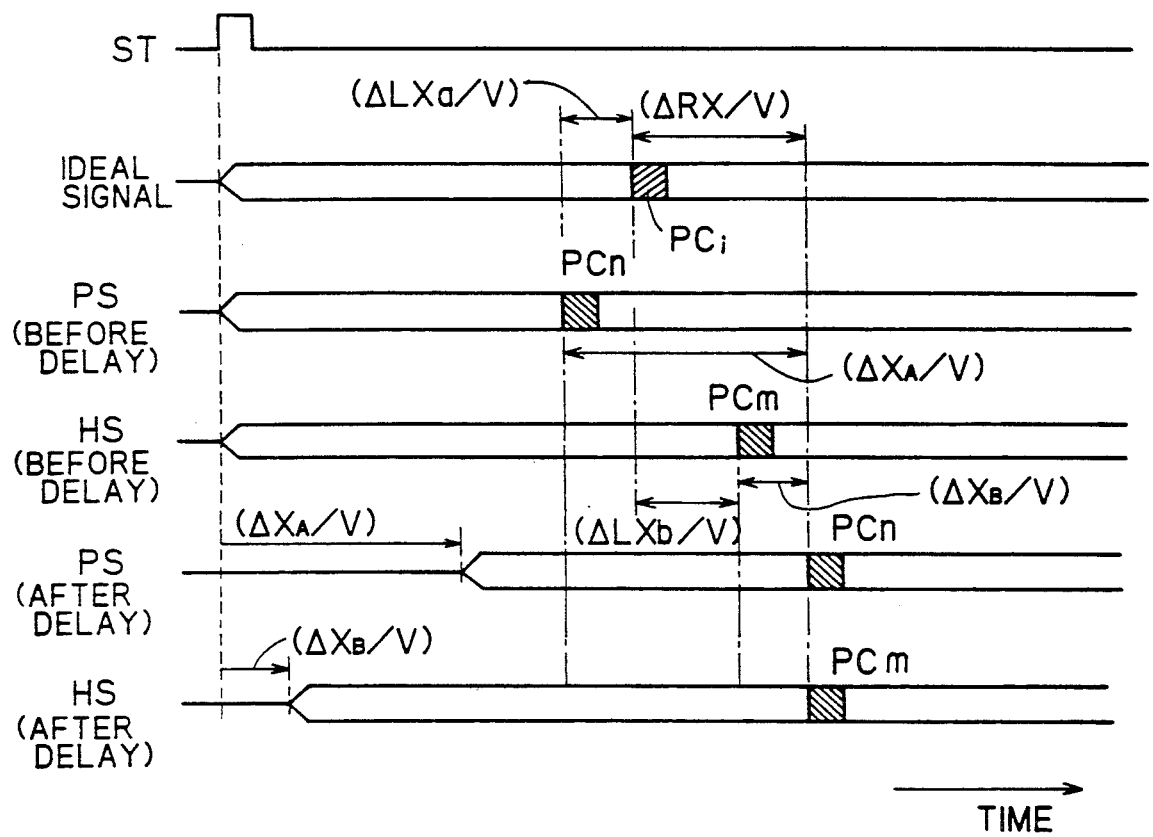

FIG. 9C is a time chart illustrating the delay processing. When a start pulse (or a main scanning start pulse) ST indicative of the reading-start of CCD photo-electric electric signals from the linear image sensors 161 and 162 is generated, the pattern signal PS and hole signal HS before delay are provided. The pattern signal PS and the hole signal HS are delayed respectively for the following time periods:

$$(\Delta X_Z/V), (\Delta X_B/V) \tag{8}$$

where V is a output rate of the CCD photo-electric signals from the linear image sensors 161 and 162 or a main scanning rate. This affords the simultaneous provision of the photo-electric signals from the read pixels $PC_n$ and $PC_m$ corresponding to the same pixel PX (FIGS. 9A and 9B).

Similarly to the reference position $RLX_i$ (of FIG. 9B) for the i-th CCD cell, reference positions for the other CCD cells can be determined. The width $2\Delta RX$ of the X-tolerance is common to the respective CCD cells. Inasmuch as the mounting errors of the respective linear image sensors 161 and 162 included in the optical heads H0 to H7 are similar to each other, the width $2\Delta RX$ of the X-tolerance is common to the optical heads H0 to H7. Further, since the mounting errors in other devices of the same type as the pattern inspection device 10 are similar to each other, the width $2\Delta RX$ can be determined for the respective devices in common. By the aforesaid delay processing, the output signals of the optical heads H0 to H7 can be converted into signals equivalent to those which can be obtained by reading at the reference position defined according to a common rule. As a result, the matching between the image signals and the interchangeability of the image data between the pattern inspection devices of the same type can be ensured. Similarly to the sub-scanning direction, the reference position in the main scanning direction may be set behind the X-tolerance as viewed in the main scanning direction.

D-3. Measurement of Deviation in Reading-Position

For execution of the aforesaid delay, the delay amounts of the output signals must be determined for each of the linear image sensors 161 and 162 included in the optical heads H0 to H7. The main scanning rate and a sub-scanning rate in the image reading of the printed circuit board 20 have respective predetermined values. Hence, the delay amounts can be determined if the deviations of the actual reading-positions from the reference positions in the respective scanning directions.

When the deviations $\Delta X_A$ and $\Delta X_B$ in the main scanning direction are measured for each one of the CCD photo-electric cells in the linear image sensors 161 and 162, it is unnecessary to measure the deviations in the other CCD photo-electric cells in the linear image sensors 161 and 162. The reason is that the one-dimensional arrays of the CCD photo-electric cells in the linear image sensors are formed on a single semiconductor substrate and the intervals therebetween are fixed so that the deviations of the reading pixels of the CCD photo-electric cells from the reference position have a common value equal to the error in mounting the linear image sensors to the pattern inspection device 10. It is, accordingly, sufficient to measure the deviations $\Delta X_A$ and $\Delta X_B$ in the main scanning direction for each of the optical heads H0 to H7.

The deviations $\Delta C_{A0-}$, $\Delta C_{B0-}$, $\Delta C_{A0+}$, $\neq C_{B0+}$, ... in the sub-scanning direction should be measured for each linear image sensor in the optical heads H0 to H7.

A scale plate 520 shown in FIG. 10A, for example, can be used for the measurement of the deviations from the reference position. The scale plate 520 is formed with a first marked line 522 extending in the ($\pm X$) directions and eight second marked lines 523 extending in the ($\pm Y$) directions both of which are drawn on the surface of a transparent flat plate 521. The intervals between the second marked lines 523 are equal to each other and are identical to the arrangement intervals of the optical heads H0 to H7 in the main scanning direction.

In an adjustment process for the pattern inspection device 10, the scale plate 520 is placed on the glass plate 15. The light sources 111 to 113 for reflected illumination (of FIG. 3) and the light source 120 for transmitted illumination light up, and the movable table 13 is transferred in the (+Y) direction. The optical heads H0 to H7 read the first and second marked lines 522 and 523.

Figure 10B:
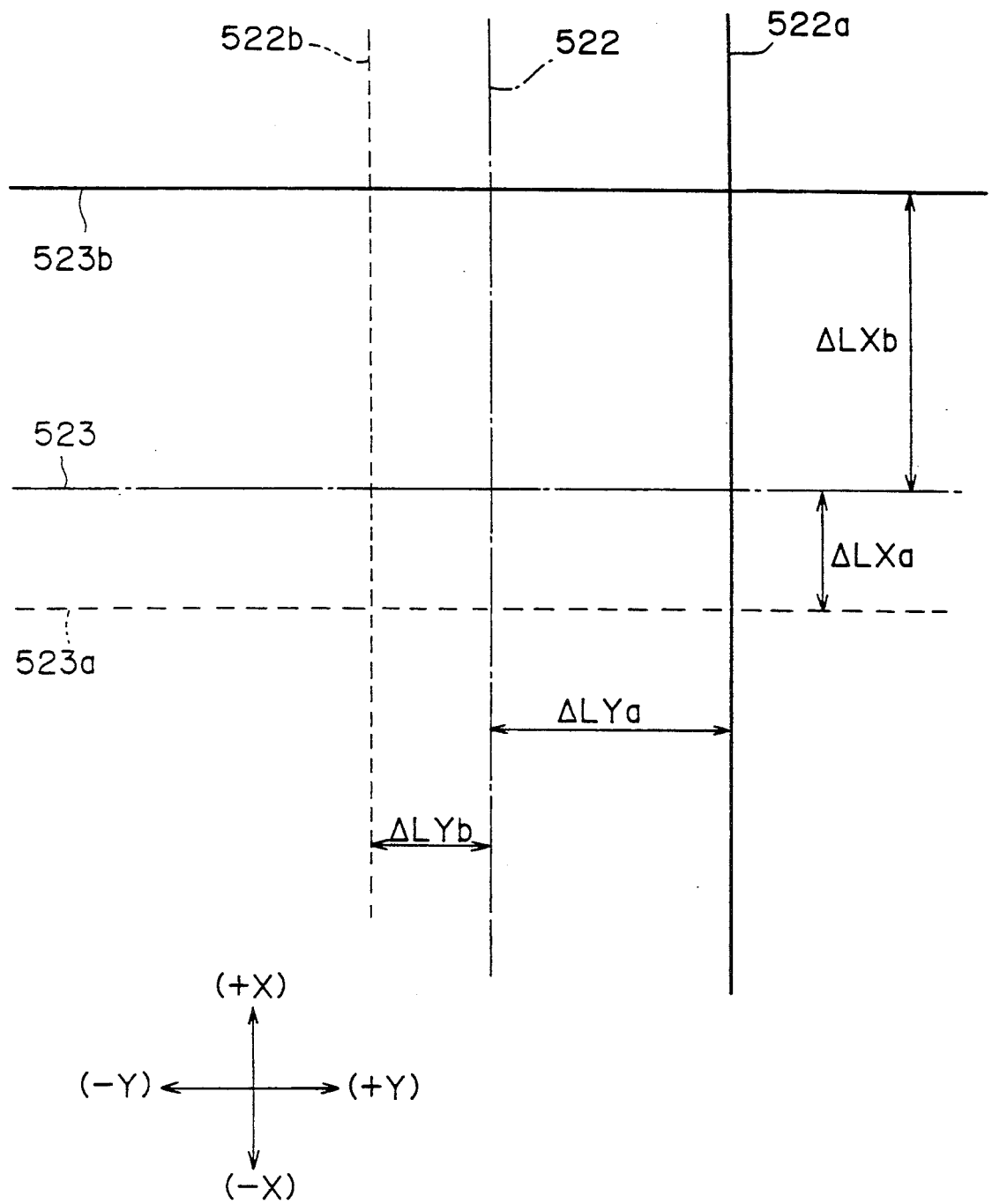

FIG. 10B shows an example of the image obtained when the optical head H0 reads the marked lines 522 and 523. The dashed-and-dotted lines of FIG. 10B represent the read images of the marked lines 522 and 523 on the supposition that the linear image sensors 161 and 162 are mounted at ideal positions in conformity with design. Because of the mounting errors of the actual linear image sensors 161 and 162, marked line images 522a and 523a which are read by the linear image sensor 161 and marked line images 522b and 523b which are read by the linear image sensor 162 deviate from the original marked lines 522 and 523. Deviations $\Delta LX_a$, $\Delta LY_a$, $\Delta LX_b$, $\Delta LY_b$ between the positions of the predetermined marked lines 522, 523 and the images 522a, 523a, 522b, 523b are calculated based on the output signals of the linear image sensors 161 and 162.

Figure 8B:
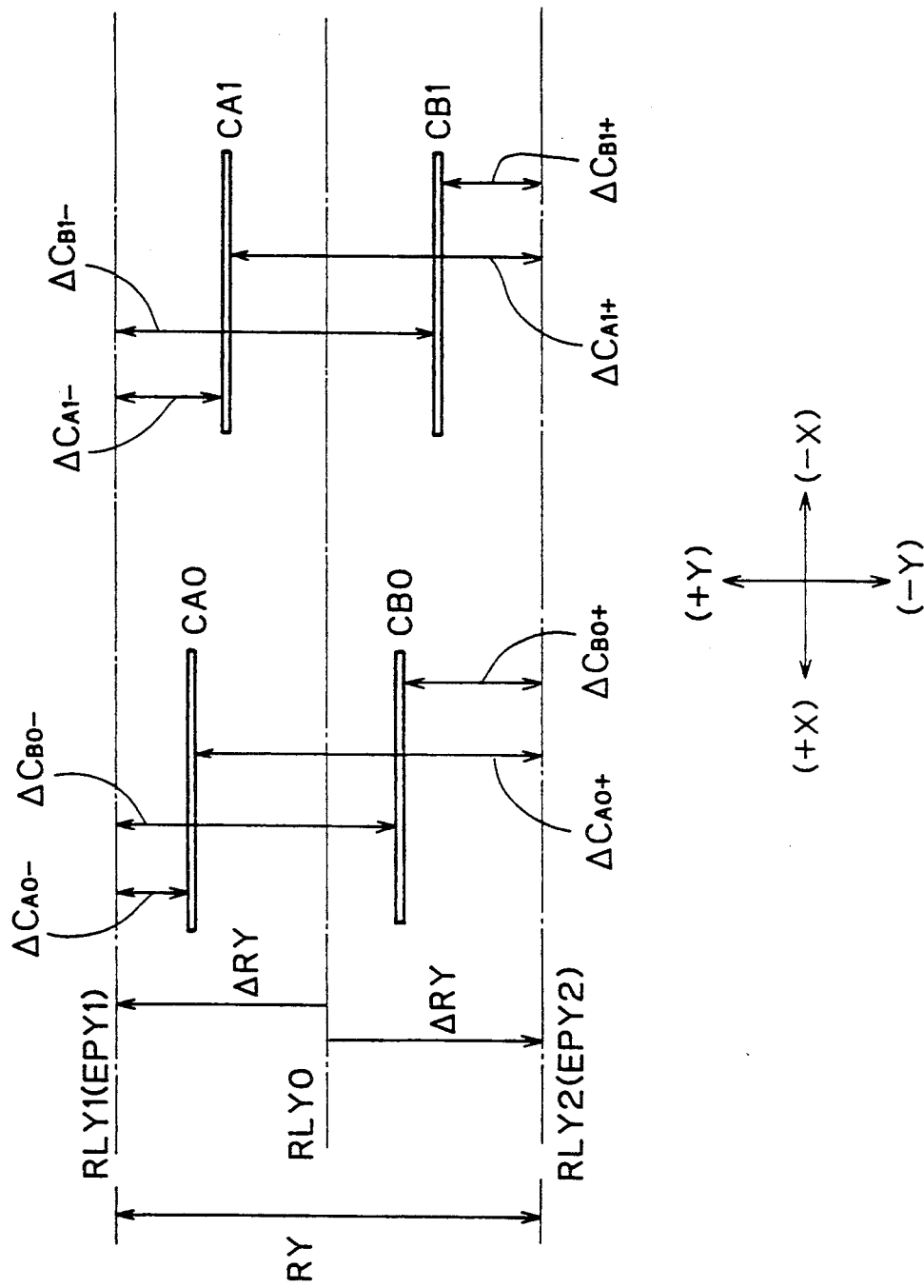

The deviations $\Delta LY_a$ and $\Delta LY_b$ correspond to the deviations between the system reference line RLY0 and the reading-positions CA0 and CB0 of FIG. 8B, while the deviations $\Delta LX_a$ and $\Delta LX_b$ correspond to the deviations between the reference line RLX0 and the read pixels $PX_A$ and $PX_B$ of FIG. 9B. Hence, the deviations $\Delta C_{A0-}$, $\Delta C_{B0-}$, $\Delta C_{A0+}$, $\Delta C_{B0+}$ (FIG. 8B) and the deviations $\Delta X_A$, $\Delta X_B$ are obtained from the following expressions (9) to (14):

$$\Delta C_{A0-} = \Delta RY - \Delta LY_a \tag{9}$$

$$\Delta C_{B0-} = \Delta RY + \Delta LY_b \tag{10}$$

$$\Delta C_{A0+} = \Delta RY + \Delta LY_a \tag{11}$$

$$\Delta C_{B0+} = \Delta RY - \Delta LY_b \tag{12}$$

$$\Delta X_A = \Delta RX + \Delta LX_a \tag{13}$$

$$\Delta X_B = \Delta RX - \Delta LX_b \tag{14}$$

The expressions (9) to (14) are those for the case where positional errors are caused in the directions shown in FIG. 10B.

Using the sub-scanning rat U and the main scanning rate V, the delay amounts (or the delay time periods) $\Delta DP_-$ and $\Delta DH_-$ for the pattern and hole signals PS and HS in the going-scan period are obtained as follows:

$$\Delta DP_- = \Delta C_{A0-}/U + \Delta X_A/V \tag{15}$$

$$\Delta DH_- = \Delta C_{B0-}/U + \Delta X_B/V \quad (16)$$

The delay time periods $\Delta DP_+$ and $\Delta DH_+$ in the return-scan period are given by the following expressions (17) and (18).

$$\Delta DP_+ = \Delta C_{A0+}/U + \Delta X_Z/V \quad (17)$$

$$\Delta DH_+ = \Delta C_{B0+}/U + \Delta X_B/V \quad (18)$$

Since the total delay time periods $\Delta DP_-$, $\Delta DH_{31}$, $\Delta DP_+$ and $\Delta DH_+$ are calculated through the additive composition of the respective delay time periods in the sub-scanning direction and in the main scanning direction, the total delay time periods can be accurately calculated where the positional deviations are present not only in either the main scanning or sub-scanning direction but also in both of the directions. The calculation of the delay time periods is conducted for each optical head or for each channel.

D-4. Alignment Circuit

Figure 11:
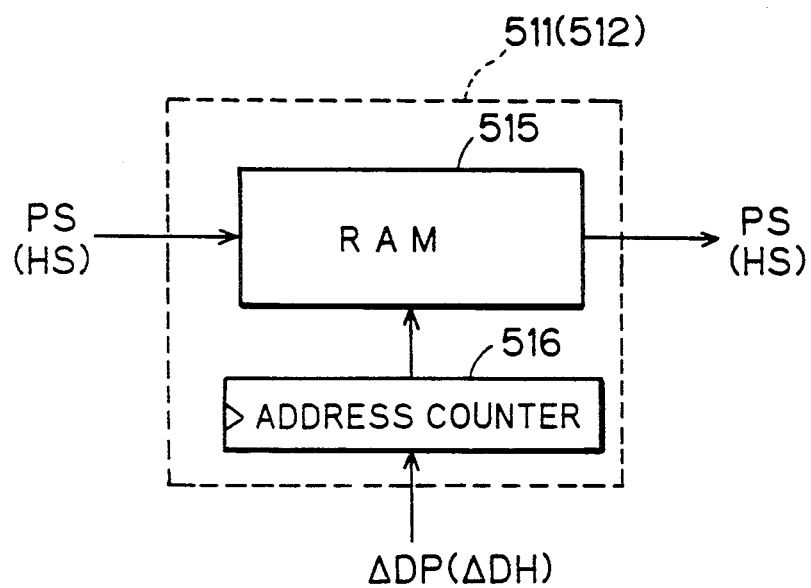
FIG. 11 shows the internal structure of a variable delay circuit.

Referring to FIG. 6 again, the pattern signal PS and the hole signal HS are given to variable delay circuits 511 and 512 both included in the alignment circuit 510, respectively. Each of the variable delay circuits 511 and 512 includes a RAM 515 and an address counter 516 both for performing delay processing through temporary storage of the signals PS and HS, as shown in FIG. 11. The values of the delay times $\Delta DP_-$, $\Delta DH_-$, $\Delta DP_+$ and $\Delta DH_+$ are previously determined and stored in a delay time register 513 shown in FIG. 6.

The synchronization control circuit 314 of FIG. 4 generates a scanning direction indication signal indicative of whether the read scanning to be now executed is the going-scan or the return-scan to deliver the signal to a read control circuit 514 shown in FIG. 6. The read control circuit 514 produces a switching signal SW in response to the scanning direction indication signal and applies the signal SW to the delay time register 513, whereby the delay time values $\Delta DP_-$ and $\Delta DH_-$, if in the going-scan, or the delay time values $\Delta DP_+$ and $\Delta DH_+$, if in the return-scan, are applied to the variable delay circuits 511 and 512 as delay time values $\Delta DP$ and $\Delta DH$, respectively.

Figure 12:
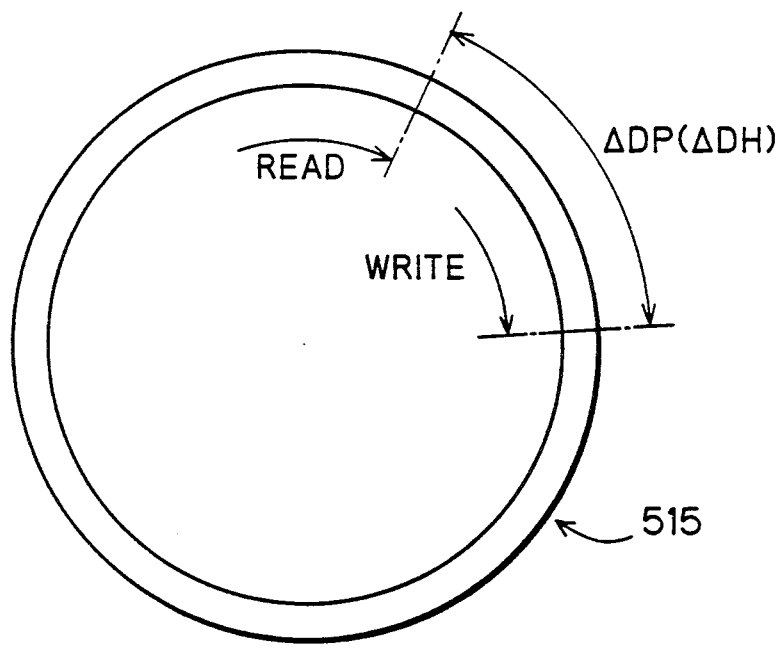
FIG. 12 illustrates a signal delay using a RAM.

The address counter 516 receives the delay time value $\Delta DP$ (or $\Delta DH$) to control the read/write address of the RAM 515 such that the difference between the write-address and the read-address in the RAM 515 is always equal to the delay time value $\Delta DP$ (or $\Delta DH$). This control is conceptually shown in FIG. 12. The storage region of the RAM 515 is used cyclically. The difference in progress between the writing and the reading indicated by the clockwise arrows of FIG. 12 corresponds to the delay time value $\Delta DP$ (or $\Delta DH$). The variable delay circuits 511 and 512 receive the pattern signal PS and the hole signal HS and delay the signals PS and HS for the delay times $\Delta DP$ and $\Delta DH$ to output the delayed signals to an inspection circuit (not shown), respectively.

When the scanning direction indication signal indicates the inversion of the sub-scanning direction, the delay time values $\Delta DP$ and $\Delta DH$ is switched from $\Delta DP_-$ and $\Delta DH_-$ to $\Delta DP_+$ and $\Delta DH_+$, or from the latter to the former. The inspection circuit may be a circuit structured in accordance with a comparative inspection method or a DRC method (Design Rule Check Method). The former method is known in the art and is disclosed in Japanese Patent Laid-Open Gazette No. 60-263807 (1985) and the latter method is disclosed in Japanese Patent Laid-Open Gazette No. 57-149905 (1982), for example.

The alignment circuit 510 thus converts the output signals of the linear image sensors 161 and 162 for each channel into image signals which are excellent in matching with each other and in interchangeability with other devices of the same type.

Figure 13:
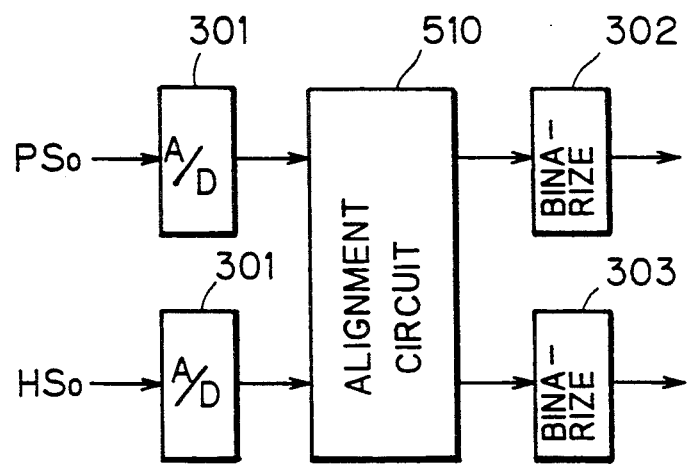
Figure 14:
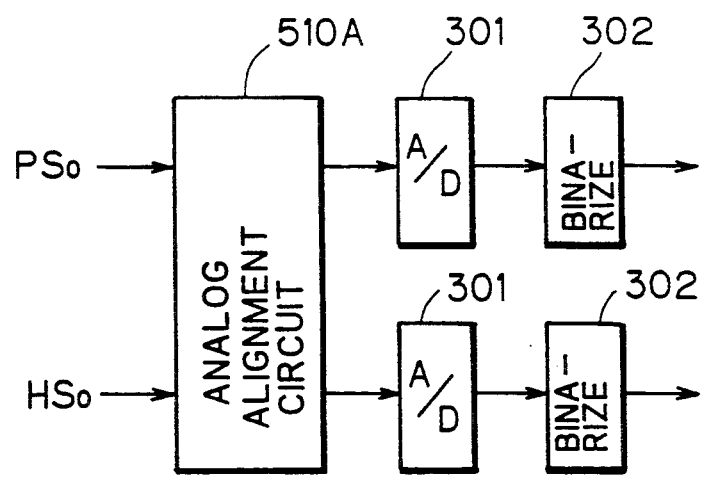

E. Other Preferred Embodiments (1) The alignment circuit 510 may be disposed in an arbitrary position between the inspection circuit and the linear image sensors 161 and 162. In an example shown in FIG. 13, the alignment circuit 510 is provided between the A/D converters 301 and the binarizing circuits 302 and 303. In the example of FIG. 14, an analog alignment circuit 510A is provided in the immediately preceding position of the A/D converters 301.

Figure 15:
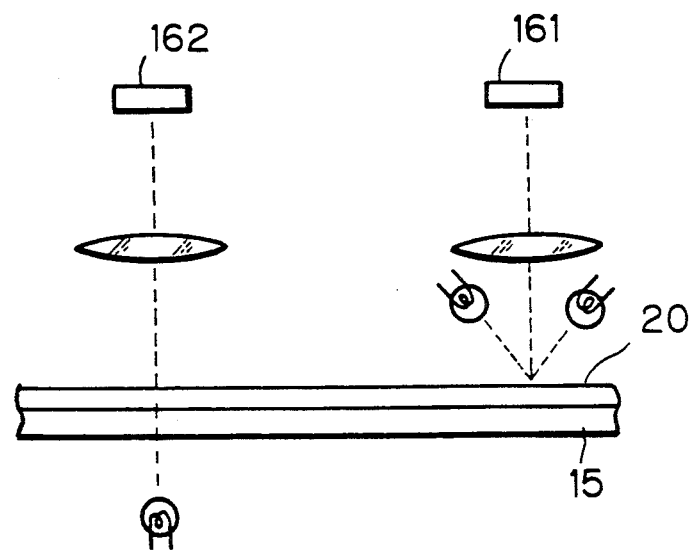
Figure 16:
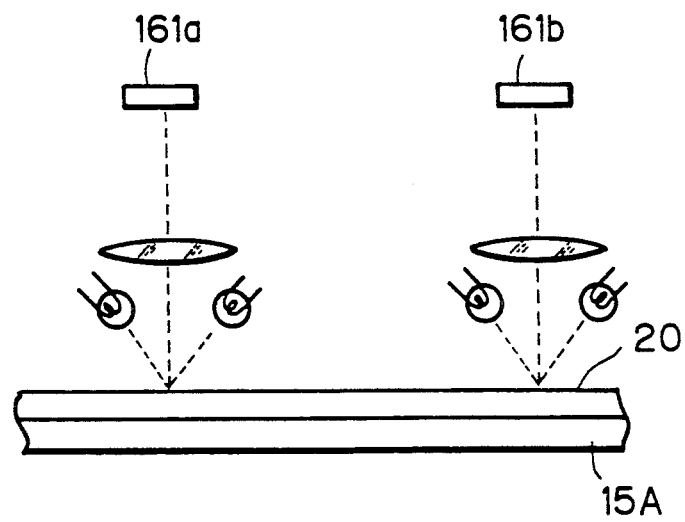
Figure 19:
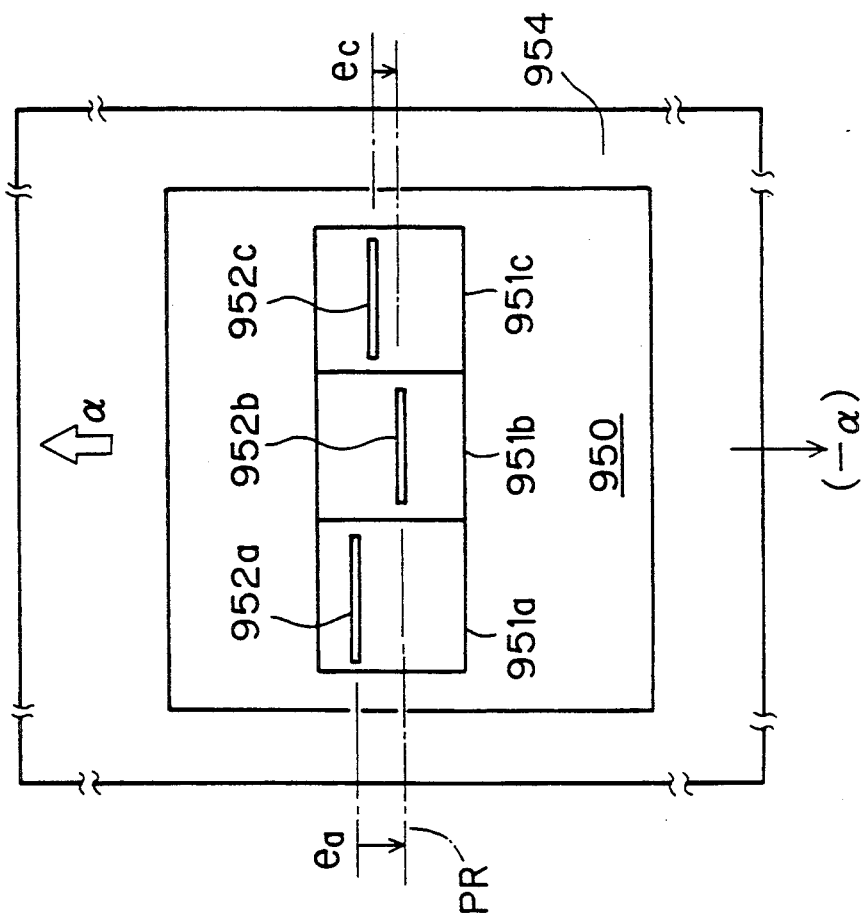
FIG. 19 illustrates the reading-position error for each channel in the pattern inspection device for the printed circuit board and an conventional method of compensating for the error.
Figure 18:
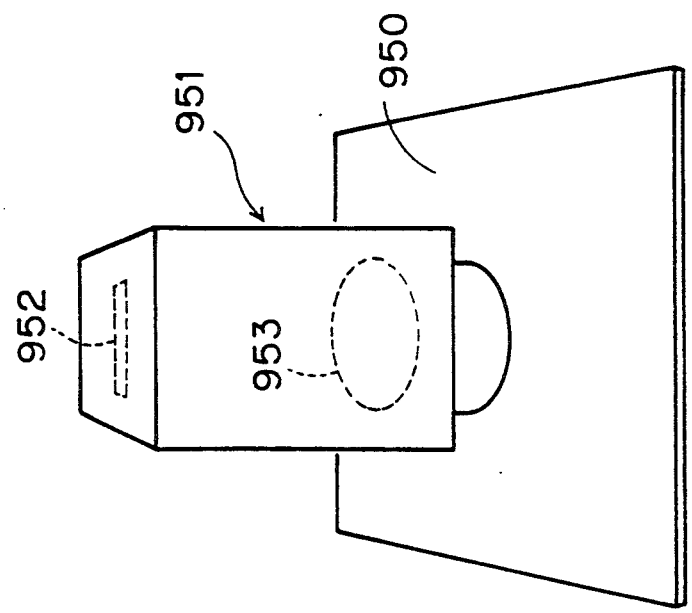
FIG. 18 is a schematic view of the optical head.

(2) FIG. 15 shows the parallel arrangement of the linear image sensor 161 for providing the pattern image by means of the light source for reflected illumination and the linear image sensor 162 for providing the hole image by means of the light source for transmitted illumination. FIG. 16 shows the parallel arrangement of two linear image sensors 161a and 161b using the light sources for reflected illumination to carry out the pattern inspection. Both of the examples are capable of compensating for the reading-position errors according to the present invention.

(3) FIG. 17 is a schematic plan view of two pattern inspection devices 10a and 10b of the same type, each of which is a mono-channel device including a single optical head H. The optical head H is equipped with a single linear image sensor IMS. Also practically useful is the application of the present invention to this example. Reference positions RL1 and RL2 respectively for the going- and return-scans are determined. The output signals of the linear image sensors IMS are delayed to the reference positions RL1 and RL2. This delay processing permits the image data produced in one of the devices 10a and 10b to be used intactly in the other device. In this case, the reference positions RL1 and RL2 must be common to the devices 10a and 10b.

The present invention is particularly effective for a system including a plurality of image sensors. However, the application of the present invention to a system including a single image sensor affords an improvement in the interchangeability of the image information with other systems of the same type.

(4) The image sensor to which the present invention is applied may be not only the linear image sensor but also a two-dimensional image sensor. The present invention is applicable to various image scan readers such as a process scanner of a flat bed type in addition to the pattern inspection device for the printed circuit board.

While the invention has been shown and described in detail, the foregoing description is in all aspects illustrative and not restrictive. It is therefore understood that numerous modifications and variations can be devised without departing from the scope of the invention.

We claim:

1. A method of compensating for a positional error in reading an image of an objective material with an image scan system having at least one image sensor, wherein said image scan system is operable to read said image while scanning said objective material in an image-scanning direction, said method comprising the steps of:

(a) on said image scan system, determining a positional tolerance range for an image reading position of said image sensor, wherein
said image reading position of said image sensor is included in said positional tolerance range, and
said positional tolerance range has such a front end and a rear end that a direction from said rear end to said front end is in parallel with said image-scanning direction;

(b) determining a reference position on said rear end or behind said rear end with respect to said image-scanning direction;

(c) measuring a positional deviation between said image reading position of said image sensor and said reference position;

(d) reading said image of said objective material with said image sensor while scanning said objective material in said image-scanning direction to obtain an image signal representative of said image of said objective material; and (e) delaying said image signal by a delay time proportional to said positional deviation to compensate for a positional error in reading said image of said objective material.

2. The method of claim 1, wherein
the step (a) comprises the step of:
(a-1) determining said positional tolerance range so that said positional tolerance range is symmetrical with respect to a pre-designed ideal image reading position of said image sensor;
the sep (b) comprises the steps of:
(b-1) selecting said image-scanning direction in parallel with a predetermined first direction and determining said reference position on said rear end or behind said rear end with respect to said first direction, to thereby obtain a first reference position; and
(b-2) selecting said image-scanning direction in parallel with a second direction which is the reverse of said first direction and determining said reference position on said rear end or behind said rear end with respect to said second direction, to thereby obtain a second reference position;
the step (c) comprises the steps of:
(c-1) measuring a first positional deviation between said image reading position of said image sensor and said first reference position; and
(c-2) measuring a second positional deviation between said image reading position of said image sensor and said second reference position;
the step (d) comprises the steps of:
(d-1) reading said image of said objective material with said image sensor while scanning said objective material in said first direction to obtain a first image signal representative of a first part of said image of said objective material; and
(d-2) reading said image of said objective material with said image sensor while scanning said objective material in said second direction to obtain a second image signal representative of a second part of said image of said objective material; and
the step (e) comprises the steps of:
(e-1) delaying said first image signal by a first delay time proportional to said first positional deviation to compensate for a positional error in reading said image of said objective material in said first direction; and (e-2) delaying said second image signal by a second delay time proportional to said second positional deviation to compensate for a positional error in reading said image of said objective material in said second direction.

3. The method of claim 2, wherein
the step (c) comprises the steps of:
(c-3) preparing a sheet member on which a line mark is provided;
(c-4) reading an image of said sheet member with said image sensor; and
(c-5) obtaining a distance between a position of said line mark in said image of said sheet member and a position of said line mark which is predetermined under the assumption that said image reading position of said image sensor is just on said pre-designed ideal image reading position, to thereby obtain said positional deviation.

4. The method of claim 3, wherein
said image scan reader comprises a plurality of image sensors;
the step (a) comprises the step of:
(a-2) determining said positional range in common to said plurality of image sensors; and
the step (b) comprises the step of:
(b-3) determining said reference position in common to said plurality of image sensors;
said method further comprising the step of:
(f) conducting the steps (c), (d) and (e) for each one of said plurality of image sensors.

5. The method of claim 4, wherein
said objective material is a printed board on which a conductive pattern is provided and through which a through hole is formed; and
said plurality of image sensors include first and second linear image sensors each of which extends in a direction perpendicular to said image-scanning direction and which are arranged in parallel with each other with an arrangement gap therebetween;
the step (D) comprises the steps of:
(d-3) applying a first light having a first optical character to said conductive pattern;
(d-4) applying a second light having a second optical character to said through hole;
(d-5) detecting said first light reflected on said conductive pattern with said first linear image sensor to obtain a pattern signal representative of said conductive pattern; and
(d-6) detecting said second light passing through said through hole with said second linear image sensor to obtain a hole signal representative of said through hole; and
the step (e) comprises the steps of:
(e-3) delaying said pattern image by a first delay time proportional to a first deviation between an image reading position of said first image sensor and said reference position to compensate for said first deviation; and
(e-4) delaying said hole image by a second delay time proportional to a second deviation between an image reading position of said second image sensor and said reference position to compensate for said second deviation.

6. A method of compensating for a positional error in reading an image of an objective material with an image scan system having at least one image sensor, wherein said image scan system is operable to read said image while scanning said objective material in a main scanning direction and a subscanning direction, said method comprising the steps of:

(a) on said image scan system, determining first and second positional tolerance ranges for an image reading position of said image sensor, wherein said first and second positional tolerance ranges are determined in said main scanning and subscanning directions, respectively, said image reading position of said image sensor is included in said first and second positional tolerance ranges in main scanning and subscanning directions, respectively, said first positional tolerance range has such a first front end and a firs rear end that a first direction from said first rear end to said first front end is in parallel with said main scanning direction; and said second positional tolerance range has such a second front end and a second rear end that a second direction from said second rear end to said second front end is in parallel with said subscanning direction;

(b) determining such first and second reference positions that;

said first reference position is on said first rear end or behind said first rear end with respect to said main scanning direction; and said second reference position is on said second rear end or behind said second read end with respect to said subscanning direction;

(c) measuring:

a first positional deviation between said image reading position of said image sensor and said first reference position; and a second positional deviation between said image reading position of said image sensor and said second reference position;

(d) reading said image of said objective material with said image sensor while scanning said objective material in said main scanning and subscanning directions to obtain an image signal representative of said image of said objective material; and (e) delaying said image signal by a delay time proportional to a sum of said first and second positional deviations to compensate for a positional error in reading said image of said objective material.

7. The method of claim 6, wherein
said image sensor comprises a linear array of photoelectric cells; and
the step (c) comprises the step of;

(c-1) measuring a positional deviation between an image reading position of one photoelectric cell included in said linear array of photoelectric cells and said first reference position to obtain said first positional deviation.

8. The method of claim 7, wherein
the step (c) further comprises the steps of;

(c-2) calculating a first ratio of said first positional deviation and a first value representative of a main scanning rate in reading said image of said objective material;

(c-3) calculating a second ratio of said second positional deviation and a second value representative of a subscanning rate in reading said image of said objective material; and (c-4) calculating a sum of said first and second ratios to obtain said delay time.

9. An image scan reader for reading an image of an objective material while scanning said objective material in an image-scanning direction, said image scan reader comprising:

(a) at least one image sensor for reading said image of said objective material to obtain an image signal representative of said image of said objective material; and (b) delay means for delaying said image signal by a predetermined delay time to obtain a delayed image signal in which a positional error in reading said image of said objective material is compensated for;

wherein a positional tolerance range for an image reading position of said image sensor is previously determined on said image scan reader;

said positional tolerance range has such a front end and a rear end that a direction from said rear end to said front end is in parallel with said image-scanning direction;

a reference position is previously determined on said rear end or behind said rear end with respect to said image-scanning direction; and said delay time is previously determined as a function of a positional deviation between said image reading position of said image sensor and said reference position.

10. The image scan reader of claim 9, further comprising:

(c) means for relatively and reciprocally moving said image sensor and said objective material to switch said image-scanning direction within opposite directions; and (d) means for relatively moving said image sensor and said objective material in a direction perpendicular to said opposite directions in response to inversion of said image-scanning direction from one of said opposite directions to the other of said opposite directions;

wherein said positional tolerance range is symmetrical with respect to a pre-designed ideal image reading position of said image sensor;

said front end is switched with said rear end in response to said inversion of said image-scanning direction;

said reference position is determined on each side of said positional tolerance range; and said delay time has respective values in:

a first scanning of said image in which a first part of said image is scanned in said one of said opposite directions; and a second scanning of said image in which a second part of said image is scanned in the other of said opposite directions.

11. A device for inspecting a printed board, said device comprising:

(a) image reading means having at least one image sensor for reading said image of said printed board to obtain an image signal representative of said image of said printed board;

(b) means for relatively moving said image reading means and said printed board, to scan respective areas of a surface of said printed board with said image sensor;

(c) delay means for delaying said image signal by a predetermined delay time to obtain a delayed image signal in which a positional error in reading said image of said printed board is compensated for; and (d) inspection means for receiving said delayed image signal to inspect said image of said printed board as a function of said delayed image signal;

wherein a positional tolerance range for an image reading position of said image sensor is previously determined on said image reading means;

said positional tolerance range has such a front end and a rear end that a direction from said rear end to said front end is in parallel with an image-scanning direction in reading said image of said printed board;

a reference position is previously determined on said rear end or behind said rear end with respect to said image-scanning direction; and said delay time is previously determined as a function of a positional deviation between said image reading position of said image sensor and said reference position.

12. The image scan reader of claim 11, wherein said means (b) comprising:

(b-1) means for relatively and reciprocally moving said image reading means and said printed board to switch an image-scanning direction within opposite directions; and (b-2) means for relatively moving said image reading means and said printed board in a direction perpendicular to said opposite directions in response to inversion of said image-scanning direction from one of said opposite directions to the other of said opposite directions;

wherein said positional tolerance range is symmetrical with respect to a pre-designed ideal image reading position of said image sensor; and said delay time has respective values in:

a first scanning of said image in which a first part of said image is scanned in said one of said opposite directions; and a second scanning of said image in which a second part of said image is scanned in the other of said opposite directions.

13. The device of claim 12, wherein said printed board comprises an insulating plate on which a conductive pattern is provided and through which a through hole is formed;

said image reading means comprises:

(a-1) a first image sensor for reading an image of said conductive pattern to generate a pattern signal representative of said image of said conductive pattern; and (a-2) a second image sensor for reading an image of said through hole to generate a hole signal representative of said image of said through hole; and said delay means comprises:

(c-1) pattern signal delay means for delaying said pattern signal by a first delay time to obtain a delayed pattern signal in which a first positional error in reading said image of said conductive pattern is compensated for; and (c-2) hole signal delay means for delaying said hole signal by a second delay time to obtain a delayed hole signal in which a second positional error in reading said image of said through hole is compensated for;

wherein said first delay time is determined in proportion to a first deviation between an image reading position of said first image sensor and said reference position; and said second delay time is determined in proportion to a second deviation between an image reading position of said second image sensor and said reference position.

14. The device of claim 13, wherein said pattern image signal delay means comprises:

(c-1-1) first memory means for temporarily storing said pattern signal; and (c-1-2) means for reading said pattern signal from said first memory means when said first delay time has passed after storage of said pattern signal in said first memory means; and said hole image signal delay means comprises:

(c-2-1) second memory means for temporarily storing said hole signal; and (c-2-2) means for reading said hole signal from said second memory means when said second delay time has passed after storage of said hole signal in said second memory means.

15. A device for inspecting a printed board, comprising:

(a) movable table means on which said printed board is placed and movable in horizontal directions;

(b) a plurality of optical heads aligned on said movable table means, each of said plurality of optical heads comprising:

(b-1) at least one image sensor for reading a partial image of said printed board to obtain a partial image signal resentative of said partial image of said printed board;

(c) a plurality of delay means assigned to said plurality of optical heads, respectively, each of said plurality of delay means comprising:

(c-1) means for receiving said partial image signal from corresponding one of said plurality of optical heads and for delaying said partial image signal by a predetermined delay time to obtain a delayed partial image signal in which a positional error in reading said image of said printed board with corresponding one of said plurality of optical heads is compensated for; and (d) inspection means for receiving respective delayed partial image signals from said means (c-1) to inspect said image of said printed board as a function of said respective delayed partial image signals;

wherein a positional tolerance range for an image reading position of said image sensor is previously determined on each of said said image scan reader;

said positional tolerance range has such a front end and a rear end that a direction from said rear end to said front end is in parallel with said image-scanning direction;

a reference position is previously determined on said rear end or behind said rear end with respect to said scanning direction; and said delay time is previously determined as a function of a positional deviation between said image reading position of said image sensor and said reference position.

16. The device of claim 15, wherein said printed board comprises an insulating plate on which a conductive pattern is provided and through which through holes are formed;

said at least one image sensor comprises:

(b-1-1) a first image sensor for reading a partial image of said conductive pattern to generate a partial pattern signal representative of said partial image of said conductive pattern; and (b-1-2) a second image sensor for reading a partial image of said through holes to generate a partial hole signal representative of said partial image of said through holes; and said means (c-1) comprises:

(c-1-1) pattern signal delay means for delaying said partial pattern signal by a first delay time to obtain a delayed partial pattern signal in which a first positional error in reading said partial image of said conductive pattern is compensated for; and (c-1-2) hole signal delay means for delaying said partial hole signal by a second delay time to obtain a delayed partial hole signal in which a second positional error in reading said partial image of said through hole is compensated for;

wherein said first delay time is determined in proportion to a first deviation between an image reading position of said first image sensor and said reference position; and said second delay time is determined in proportion to a second deviation between an image reading position of said second image sensor and said reference position.

* * * * *